(12) United States Patent
Laufer et al.

(10) Patent No.: US 10,875,863 B2
(45) Date of Patent: Dec. 29, 2020

(54) RIPK2 INHIBITORS AND METHOD OF TREATING CANCER WITH SAME

(71) Applicant: University Health Network, Toronto (CA)

(72) Inventors: Radoslaw Laufer, Oakville (CA); Grace Ng, Markham (CA); Richard Brokx, Toronto (CA); Heinz W. Pauls, Oakville (CA); Sze-Wan Li, Toronto (CA); Jacqueline M. Mason, Toronto (CA); Mark R. Bray, Oakville (CA)

(73) Assignee: UNIVERSITY HEALTH NETWORK, Toronto (CA)

(*) Notice: Subject to any disclaimer, the term of this patent is extended or adjusted under 35 U.S.C. 154(b) by 0 days.

(21) Appl. No.: 16/258,753

(22) Filed: Jan. 28, 2019

(65) Prior Publication Data

US 2019/0225617 A1   Jul. 25, 2019

Related U.S. Application Data

(63) Continuation of application No. 15/521,895, filed as application No. PCT/CA2015/051024 on Oct. 9, 2015, now Pat. No. 10,239,881.

(60) Provisional application No. 62/068,985, filed on Oct. 27, 2014.

(51) Int. Cl.
| | | |
|---|---|---|
| *C07D 487/04* | (2006.01) | |
| *A61K 31/519* | (2006.01) | |
| *A61K 45/06* | (2006.01) | |
| *A61P 37/06* | (2006.01) | |
| *A61P 29/00* | (2006.01) | |
| *A61P 35/00* | (2006.01) | |

(52) U.S. Cl.
CPC .......... *C07D 487/04* (2013.01); *A61K 31/519* (2013.01); *A61K 45/06* (2013.01); *A61P 29/00* (2018.01); *A61P 35/00* (2018.01); *A61P 37/06* (2018.01)

(58) Field of Classification Search
CPC .................................................. C07D 487/04
See application file for complete search history.

(56) References Cited

U.S. PATENT DOCUMENTS

| | | |
|---|---|---|
| 6,552,192 B1 | 4/2003 | Hanuset et al. |
| 8,354,408 B2 | 1/2013 | Bourke et al. |
| 2018/0282335 A1 | 10/2018 | Laufer et al. |

FOREIGN PATENT DOCUMENTS

| | | |
|---|---|---|
| WO | 1999/40091 A1 | 8/1999 |
| WO | 2001/70743 A1 | 9/2001 |
| WO | 2009/062258 A1 | 5/2009 |
| WO | 2010/021934 A2 | 2/2010 |
| WO | 2010/046215 A2 | 4/2010 |
| WO | 2011/079231 A1 | 6/2011 |
| WO | 2011140442 A1 | 11/2011 |
| WO | 2012/104388 A1 | 8/2012 |
| WO | 2012/122011 A2 | 9/2012 |
| WO | 2013/078254 A1 | 5/2013 |

OTHER PUBLICATIONS

Supplementary European Search Report for Application No. 15855932.8, dated Mar. 27, 2018. 7 pages.

*Primary Examiner* — Brian E McDowell
(74) *Attorney, Agent, or Firm* — McCarter & English, LLP; Steven G. Davis; Wei Song

(57) ABSTRACT

The invention is a compound represented by Structural Formula (I):

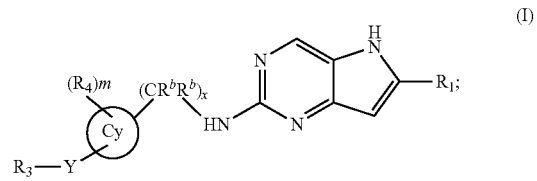

or a pharmaceutically acceptable salt thereof. Values for the variables are provided herein. Also included is a pharmaceutical composition comprising the compound represented by Structural Formula (I) and a pharmaceutically acceptable carrier or diluent and methods of treating a subject with cancer with the compound of Structural Formula (I).

15 Claims, 3 Drawing Sheets

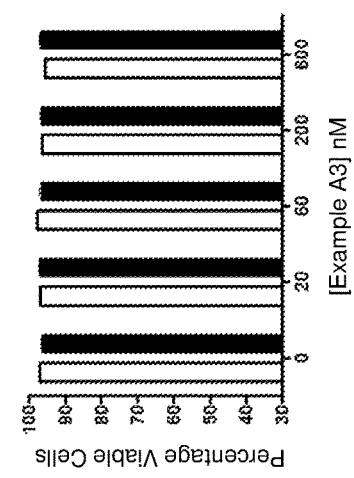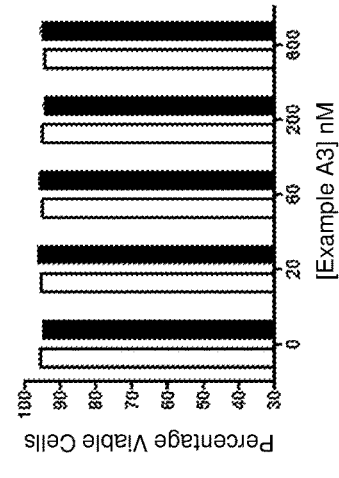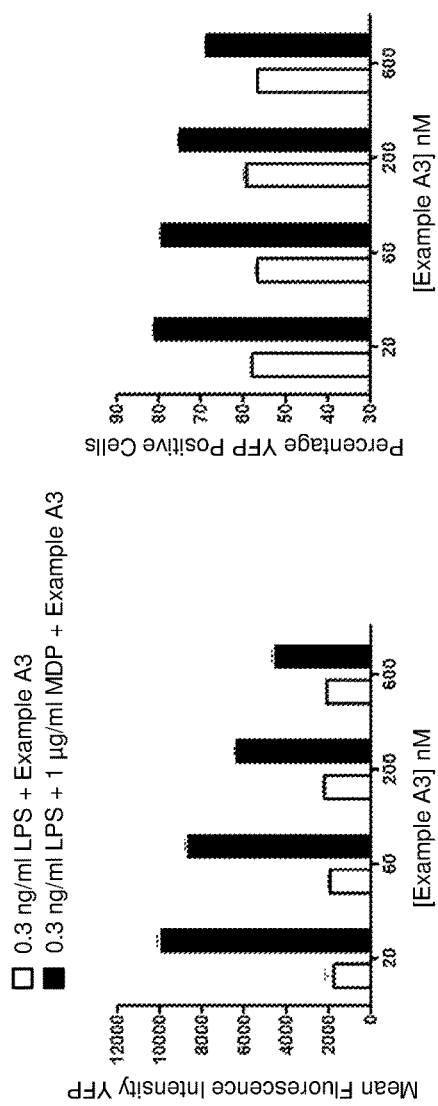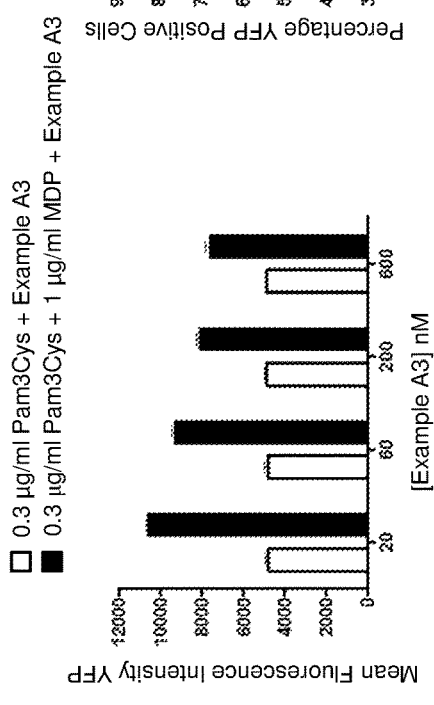
FIG. 2A
FIG. 2B

RIPK2 INHIBITORS AND METHOD OF TREATING CANCER WITH SAME

RELATED APPLICATIONS

This application is a divisional of U.S. application Ser. No. 15/521,895, filed on Apr. 26, 2017. U.S. application Ser. No. 15/521,895, is the U.S. national stage filing under 35 U.S.C. § 371(c), of International Application No. PCT/CA2015/051024, filed on Oct. 9, 2015, which claims the benefit of U.S. Provisional Application No. 62/068,985, filed Oct. 27, 2014. The entire teachings of the aforementioned applications are incorporated herein by reference.

BACKGROUND

Receptor-interacting serine/threonine-protein kinase 2 (RIPK2, also called RICK, RIP2, CARDIAK, and CARDS) has been implicated in a variety of functions including: integrating signals for innate and adaptive immune systems, regulating apoptosis, controlling a myogenic differentiation checkpoint, and regulating nuclear-factor-kappa-beta (NFkB) and Jun N-terminal kinase (JNK) activation. RIPK2 is composed of an N-terminal serine/threonine kinase catalytic domain and a C-terminal region containing a caspase activation and recruitment domain (CARD).

RIPK2 physically interacts with CLARP, a caspase-like molecule known to bind to Fas-associated protein with death domain (FADD) and caspase-8. Expression of RIPK2 promoted the activation of caspase-8 and potentiated apoptosis induced by Fas ligand, FADD, CLARP, and caspase-8. Deletion mutant analysis revealed that both the kinase domain and caspase-recruitment domain were required for RIPK2 to promote apoptosis. Significantly, expression of a RIPK2 mutant in which the lysine of the putative ATP-binding site at position 38 was replaced by a methionine functioned as an inhibitor of CD95-mediated apoptosis. Thus, RIPK2 represents a novel kinase that may regulate apoptosis induced by the CD95/Fas receptor pathway.

Because expression of RIPK2 affects the regulation of apoptosis in a variety of cell types, RIPK2 activity may be an important factor in the development of disease states in which regulation of apoptosis is critical. Significantly, RIPK2 protein level is increased in the frontal cortex of patients with Alzheimer's disease (Engidawork et. al., 2001, Biochem. Biophys. Res. Commun. 281: 84-93).

Analysis of RIPK2 deficient mice indicates that RIPK2 is required for regulation of innate and adaptive immune and inflammatory responses. RIPK2 deficient mice were born in the expected Mendelian ratio, and showed no gross developmental abnormalities or abnormal composition of lymphocytes as determined by flow cytometry (Kobayashi et. al., 2002, Nature 416: 194-199; Chin et. al., 2002, Nature 416: 190-194). However, these mice exhibited a decreased ability to defend against infection by the intracellular pathogen Listeria monocytogenes (Chin et. al., 2002). RIPK2 deficient macrophages and T-cells showed severely reduced NFkB activation (Kobayashi et. al., 2002; Chin et. al., 2002). RIPK2 deficiency also resulted in impaired interferon-.gamma. production in both T.sub.H1 and natural killer cells and impaired T.sub.H1-cell differentiation (Kobayashi et. al., 2002; Chin et. al., 2002). Analysis of RIPK2 deficient mice suggests that RIPK2 is a candidate target for immune intervention.

RIPK2 has been reported to physically associate with several proteins involved in receptor mediated signaling through the tumor necrosis factor (TNF) family of receptors including TNFR-1, TNFR-2, Fas (CD-95/APO-1), lyphotoxin-.beta. receptor, CD40, CD30, OX-40, DR3, DR4, and DR5. For example, RIPK2 physically interacts with CLARP, a caspase-related protein that interacts with Caspase-8 and FADD (a protein which associates with the Fas/CD-95 and TNFR-1 receptors) (Inohara et. al., 1998). CLARP could therefore function as an adapter molecule to link RIPK2 to proximal components of the receptor signaling complex.

RIPK2 also physically interacts with Caspase-1 (Thome et. al., 1998; Humke et. al, 2000, Cell 103: 99-111). This protein interaction is mediated by CARD domains in the C-terminus of RIPK2 and in the prodomain of Caspase-1 (Thome et. al., 1998; Humke et. al., 2000). RIPK2 enhances the activation of Caspase-1 by promoting its oligomerization which leads to processing of adjacent pro-Caspase-1 protein (Humke et. al., 2000). The association between RIPK2 and Caspase-1 can be abrogated by the ICEBERG protein, which inhibits and/or displaces RIPK2 by binding Caspase-1 through its own CARD domain. (Humke et. al., 2000).

RIPK2 has been reported to associate directly with p75 receptor in a nerve growth factor (NGF) dependent fashion (Khursigara et. al., 2001) and with several receptor associating proteins including TRAF1, TRAF2, TRAF5, and TRAF6 (Thome et. al., 1998; McCarthy et. al., 1998). Co-expression of CD40 receptor, RIPK2, TRAF1 and TRAF2 resulted in association of RIPK2 with CD40 (McCarthy et. al., 1998). Likewise, co-expression of TNFR-1 receptor, RIPK2, TRADD, TRAF1 and TRAF2 resulted in association of RIPK2 with TNFR-1 (McCarthy et. al., 1998). Collectively, these data suggest that RIPK2 is a component of the p75, CD40, Fas/CD-95 and TNFR-1 receptor signaling complexes.

RIPK2 activity appears to be altered by interaction with ligands. For example, expression of polypeptides comprising CARD domains with high affinity for RIPK2 protein binding partners may prevent RIPK2 from physically associating with other CARD domain containing proteins (Humke et. al., 2000). Protein-protein interactions mediated by CARD domains have also been reported to be disrupted by nitric oxide (NO) (Zech et. al., 2003, Biochem J. 371(Part 3): 1055-64). Compounds that alter the serine-kinase activity of RIPK2 may also influence RIPK2 function. Methods for assessing the kinase activity of RIPK2 have been described (Inohara et. al., 1998; Thome et. al., 1998; McCarthy et. al., 1998; Navas et. al., 1999). Methods for screening for compounds that modulate serine-threonine kinase activity have been disclosed (US2003/0134310A1; WO 02/14542). In addition, anti-sense oligonucleotides designed to inhibit RIPK2 have been described (U.S. Pat. No. 6,426, 221 B1).

Because of the multiple therapeutic values of compounds targeting receptor mediated signaling pathways that modulate apoptosis, cellular differentiation, and immune response, and the essential regulatory role played by RIPK2, there is a need in the art for novel compounds that can inhibit RIPK2.

SUMMARY OF THE INVENTION

Applicants have now discovered that certain pyrrolo[3,2-d]pyrimidine compounds are RIPK2 inhibitors (see Example B). Applicants have also now discovered that these pyrrolo[3,2-d]pyrimidine compounds have potent anticancer activity against breast cancer cells, colon cancer cells, and ovarian cancer cells in cell culture study (see Examples C-D); and potent anti-inflammatory/anti-autoimmune diseases (see Example E). Based on these discoveries, pyrrolo[3,2-d]pyrimidine compounds, pharmaceutical compositions thereof, and methods of treating cancer, autoinflammatory disease and autoimmune disease with the pyrrolo[3,2-d]pyrimidine compounds are disclosed herein.

One embodiment of the invention is a compound represented by Structural Formula

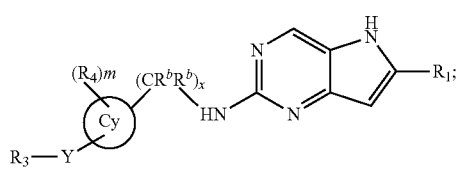

(I)

or a pharmaceutically acceptable salt thereof. Values for each of the variables are provided below.

Another embodiment of the invention is a pharmaceutical composition comprising a pharmaceutically acceptable carrier or diluent and a compound represented by Structural Formula (I) described above or a pharmaceutically acceptable salt thereof.

Another embodiment of the invention is a method of treating a subject with cancer comprising administering to the subject an effective amount of a compound of Structural Formula (I) or a pharmaceutically acceptable salt thereof.

Another embodiment of the invention is a method of treating a subject with an autoinflammatory disease comprising administering to the subject an effective amount of a compound of Structural Formula (I) or a pharmaceutically acceptable salt thereof.

Another embodiment of the invention is a method of treating a subject with an autoimmune disease comprising administering to the subject an effective amount of a compound of Structural Formula (I) or a pharmaceutically acceptable salt thereof.

Another embodiment of the invention is a method of inhibiting RIPK2 activity in a subject in need of inhibition of RIPK2 activity, comprising administering to the subject an effective amount of a compound represented by Structural Formula (I) or a pharmaceutically acceptable salt thereof.

Another embodiment of the invention is a compound represented by Structural Formula (I) or a pharmaceutically acceptable salt thereof for use in therapy. In some embodiments, the therapy is for treating a subject with cancer. In some embodiments, the therapy is for treating a subject with autoinflammatory disease. In some embodiments, the therapy is for treating a subject with autoimmune disease. Alternatively, the therapy is for inhibiting RIPK2 activity in a subject in need of inhibition of RIPK2 activity.

Another embodiment of the invention is the use of a compound represented by Structural Formula (I) or a pharmaceutically acceptable salt thereof for the manufacture of a medicament for treating a subject with cancer.

Another embodiment of the invention is the use of a compound represented by Structural Formula (I) or a pharmaceutically acceptable salt thereof for the manufacture of a medicament for treating a subject with autoinflammatory disease.

Another embodiment of the invention is the use of a compound represented by Structural Formula (I) or a pharmaceutically acceptable salt thereof for the manufacture of a medicament for treating a subject with autoimmune disease.

Another embodiment of the invention the use of a compound represented by Structural Formulas (I) or a pharmaceutically acceptable salt thereof for the manufacture of a medicament for inhibiting RIPK2 activity in a subject in need of inhibition of RIPK2 activity.

BRIEF DESCRIPTION OF THE DRAWINGS

FIG. 2A, FIG. 2B, and FIG. 2C are graphs illustrating the effects of compound A3 on cytokine production by dendritic cells. FIG. 2A shows the results of mouse bone marrow dendritic cells being stimulated for 24 hours with 0.3 ng/ml LPS±1 µg/ml MDP (i.e., NOD2 agonist) in the presence of compound A3. FIG. 2B shows the results of mouse bone marrow dendritic cells being stimulated for 24 hours with 0.3 µg/ml Pam3Cys±1 µg/ml MDP (i.e., NOD2 agonist) in the presence of compound A3. FIG. 2C shows the effect of compound A3 on the percentage of YFP positive cells (Levels of IL-12 p70, left panel), and effects on cell viability (TNFα, right panel).

DETAILED DESCRIPTION OF THE INVENTION

Figure 1:
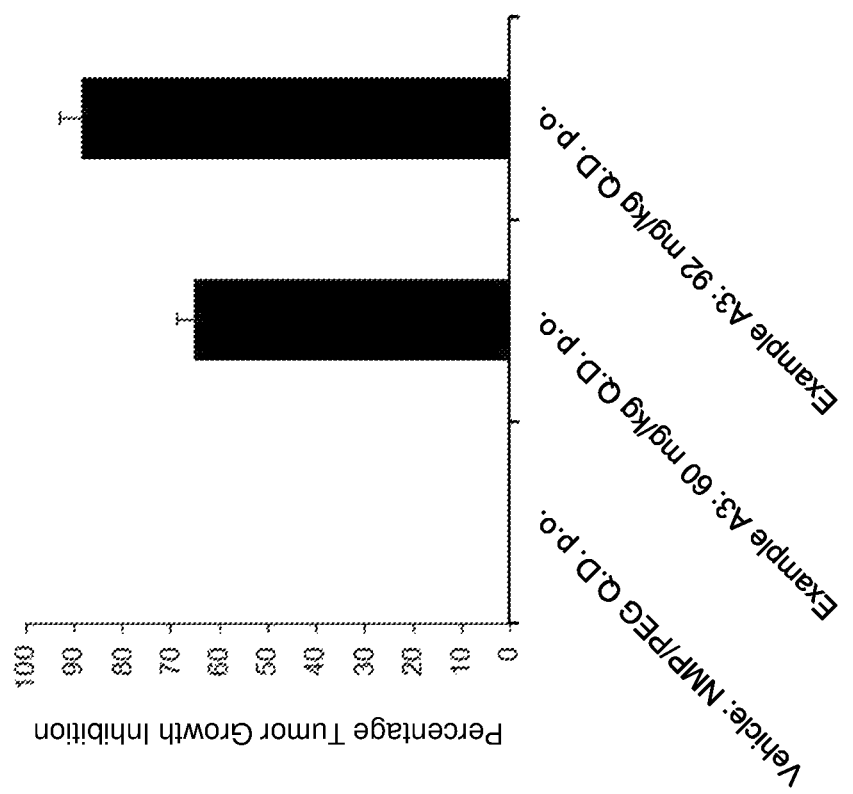
FIG. 1 is a graph illustrating in vivo responses of HCT116 xenografts in SCID mice to a treatment for 18 days with compound A3 administered at different doses (60 g/kg and 92 mg/kg Q.D. p.o.).

In a first embodiment, the invention is directed to a compound represented by Formula (I):

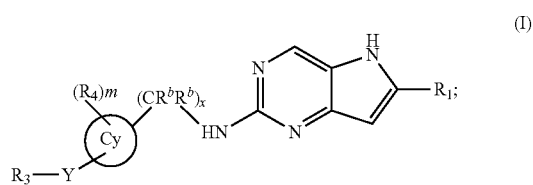

(I)

or a pharmaceutically acceptable salt thereof, wherein:
Cy is cycloaliphatic, heterocyclyl, aryl, or heteroaryl;
Y is absent, —$CR^bR^b$—, —O—, —$S(O)_n$—;
$R_1$ is cycloaliphatic, heterocyclyl, aryl or heteroaryl, each of which is optionally substituted with 1 to 3 groups individually represented by $R^a$;
$R_3$ is H, heterocyclyl or heteroaryl optionally substituted with 1 to 3 groups selected from —F, —Cl, —Br, I, —CN, —$NO_2$, —$OR^b$, —$C_1$-$C_4$alkyl, —($C_1$-$C_3$)alkylene-$OR^b$, —($C_1$-$C_3$)alkylene-$NR^bR^b$, —$C_1$-$C_4$haloalkyl, —$C_1$-$C_4$haloalkoxy, ($C_3$-$C_8$)cycloalkyl, —$NR^bR^b$, —$C(\!=\!O)NR^bR^b$, —$NR^bC(\!=\!O)NR^bR^b$, —$S(O)_nNR^bR^b$, $C(\!=\!O)OR^b$, —$OC(\!=\!O)OR^b$, —$S(O)_nR^b$, —$NR^bS(O)_nR^b$, —$C(\!=\!S)OR^b$, —$O(C\!=\!S)R^b$, —$NR^bC(\!=\!O)R^b$, —$C(\!=\!S)NR^bR^b$, —$NR^bC(\!=\!S)R^b$, —$NR^b(C\!=\!O)OR^b$, —$O(C\!=\!O)NR^bR^b$, —$NR^b(C\!=\!S)OR^b$, —$O(C\!=\!S)NR^bR^b$, —$NR(C\!=\!S)NR^bR^b$, —$C(\!=\!S)R^b$ or —$C(\!=\!O)R^b$;
each $R_4$ is independently selected from —F, —Cl, —Br, I, —CN, —$NR^bR^b$, —$OR^b$, —$C_1$-$C_4$alkyl, —($C_1$-$C_3$)alkylene-$OR^b$, —($C_1$-$C_3$)alkylene-$NR^bR^b$, —$C_1$-$C_4$haloalkyl, or —$C_1$-$C_4$haloalkoxy;
each $R^a$ is independently selected from —F, —Cl, —Br, I, —CN, $OR^b$, —$C_1$-$C_4$alkyl, ($C_2$-$C_6$)alkenyl, ($C_2$-$C_6$)alkynyl, —$C_1$-$C_4$haloalkyl, —$C_1$-$C_4$haloalkoxy, —($C_1$-$C_3$)alkylene-$OR^b$, or —($C_1$-$C_3$)alkylene-$NR^bR^b$;

each $R^b$ is independently —H or —$C_1$-$C_4$alkyl;
x is 0, 1, 2, 3, or 4;
each m is independently 0, 1, 2, or 3; and
each n is independently 0, 1, or 2.

In a second embodiment, the invention provides a compound represented by structural formula (II):

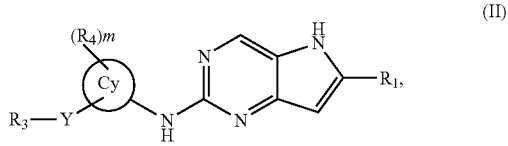

(II)

or a pharmaceutically acceptable salt thereof. Values for the variables in Structural Formulas (II) are as described for Structural Formula (I).

In a third embodiment, the invention provides a compound represented by structural formula (III):

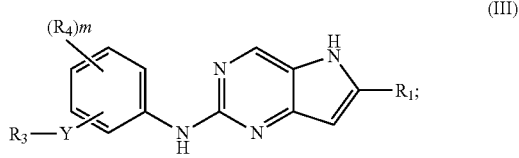

(III)

or a pharmaceutically acceptable salt thereof. Values for the variables in Structural Formulas (III) are as described for Structural Formula (I) or (II).

In a fourth embodiment, the invention provides a compound represented by structural formula (I), (II) or (III), wherein $R_1$ is optionally substituted phenyl, optionally substituted cyclopentyl, optionally substituted cyclohexyl, optionally substituted thienyl, optionally substituted pyridinyl, optionally substituted thiazolyl, optionally substituted pyrrolyl, optionally substituted imidazolyl, optionally substituted furanyl, optionally substituted oxazolyl, optionally substituted isoxazolyl, optionally substituted pyrazolyl, optionally substituted isothiazolyl, optionally substituted pyrimidinyl, optionally substituted pyrazinyl, optionally substituted pyridazinyl, optionally substituted oxadiazolyl, optionally substituted tetrahydropyranyl, optionally substituted triazolyl, or optionally substituted thiadiazolyl, and values for the remainder of the variables are as described above for Structural Formula (I), (II), or (III).

In a fifth embodiment, the invention provides a compound represented by structural formula (I), (II) or (III), wherein $R_1$ is optionally substituted phenyl, optionally substituted cyclopentyl, optionally substituted thienyl, or optionally substituted tetrahydropyranyl, and values for the remainder of the variables are as described above for Structural Formula (I), (II), or (III) or in the fourth embodiment.

In a sixth embodiment, the invention provides a compound represented by structural formula (I), (II) or (III), wherein $R_3$ is optionally substituted monocylic heterocyclyl or optionally substituted monocylic heteroaryl, and values for the remainder of the variables are as described above for Structural Formula (I), (II), or (III), or in the fourth, fifth embodiment. Alternatively, $R_3$ is optionally substituted monocylic heterocyclyl.

In a seventh embodiment, the invention provides a compound represented by structural formula (I), (II) or (III), wherein m is 0, and values for the remainder of the variables are as described above for Structural Formula (I), (II), or (III), or in the fourth, fifth, sixth embodiment.

In an eighth embodiment, the invention provides a compound represented by structural formula (I), (II) or (III), wherein $R_3$ is optionally substituted azetidinyl, optionally substituted morpholinyl, optionally substituted piperazinyl, optionally substituted piperidinyl, optionally substituted tetrahydropyranyl, optionally substituted pyrrolidinyl, optionally substituted thiomorpholinyl, optionally substituted tetrahydropyranyl, or optionally substituted tetrahydrofuranyl, optionally substituted homomorpholinyl, optionally substituted homopiperazinyl, optionally substituted thiomorpholine dioxide, or optionally substituted thienomorpholine oxide, and values for the remainder of the variables are as described above for Structural Formula (I), (II), or (III), or in the fourth, fifth, sixth, or seventh embodiment.

In a ninth embodiment, the invention provides a compound represented by structural formula (I), (II) or (III), wherein $R_3$ is optionally substituted morpholinyl, optionally substituted piperazinyl, optionally substituted piperidinyl, or optionally substituted thiomorpholinyl, and values for the remainder of the variables are as described above for Structural Formula (I), (II), or (III), or in the fourth, fifth, sixth, seventh, or eighth embodiment.

In a tenth embodiment, the invention provides a compound represented by structural formula (I), (II) or (III), wherein the compound is represented by the following structural formula:

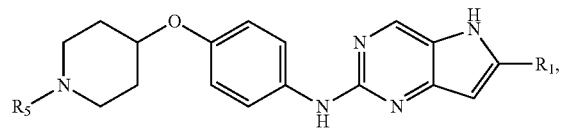

or a pharmaceutically acceptable salt thereof, wherein $R_5$ is —$C_1$-$C_4$alkyl or —($C_1$-$C_3$)alkylene-$OR^b$, and values for the remainder of the variables are as described above for Structural Formula (I), (II), or (III), or in the fourth, fifth, sixth, seventh, eighth or ninth embodiment.

In an eleventh embodiment, the invention provides a compound represented by structural formula (I), (II) or (III), wherein the compound is represented by the following structural formula:

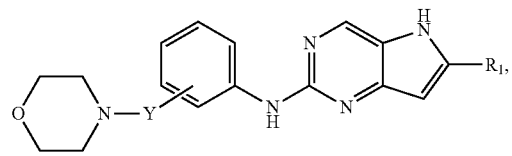

or a pharmaceutically acceptable salt thereof, wherein Y is absent or —$CH_2$—; and Y is attached to the meta or para position of the phenyl ring, and values for the remainder of the variables are as described above for Structural Formula (I), (II), or (III), or in the fourth, fifth, sixth, seventh, eighth or ninth embodiment.

In a twelfth embodiment, the invention provides a compound represented by structural formula (I), (II) or (III), wherein the compound is represented by the following structural formula:

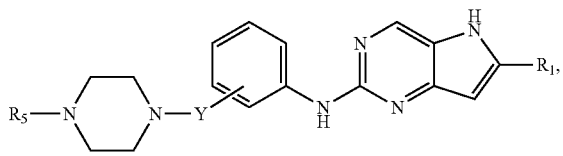

or a pharmaceutically acceptable salt thereof, wherein $R_5$ is —H, $C_1$-$C_4$alkyl, —$(C_1$-$C_3)$alkylene-$OR^b$; Y is absent or —$CH_2$—; and Y is attached to the meta or para position of the phenyl ring, and values for the remainder of the variables are as described above for Structural Formula (I), (II), or (III), or in the fourth, fifth, sixth, seventh, eighth or ninth embodiment.

In a thirteenth embodiment, the invention provides a compound represented by structural formula (I), (II) or (III), wherein $R_1$ is

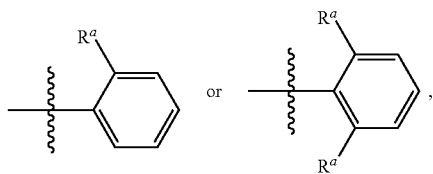

and values for the remainder of the variables are as described above for Structural Formula (I), (II), or (III), or in the fourth, fifth, sixth, seventh, eighth, ninth, tenth, eleventh, or twelfth embodiment.

In a fourteenth embodiment, the invention provides a compound represented by structural formula (I), (II) or (III), wherein each $R^a$ is independently selected from —F, —Cl, or —$CH_3$, and values for the remainder of the variables are as described above for Structural Formula (I), (II), or (III), or in the fourth, fifth, sixth, seventh, eighth, ninth, tenth, eleventh, twelfth, or thirteenth embodiment.

The invention also includes the compounds depicted by structure and/or described by name in the Exemplification. The invention includes both the neutral form of these compounds as well as pharmaceutically acceptable salts thereof. Treatments with and/or uses of these compounds includes the neutral form of these compounds as well as pharmaceutically acceptable salts thereof.

The term "alkyl" used alone or as part of a larger moiety, such as "alkoxy" or "haloalkyl" and the like, means saturated aliphatic straight-chain or branched monovalent hydrocarbon radical. Unless otherwise specified, an alkyl group typically has 1-4 carbon atoms, i.e. ($C_1$-$C_4$)alkyl. As used herein, a "($C_1$-$C_4$)alkyl" group is means a radical having from 1 to 4 carbon atoms in a linear or branched arrangement.

"Alkoxy" means an alkyl radical attached through an oxygen linking atom, represented by —O-alkyl. For example, "($C_1$-$C_4$)alkoxy" includes methoxy, ethoxy, propoxy, and butoxy.

The terms "haloalkyl" and "haloalkoxy" means alkyl or alkoxy, as the case may be, substituted with one or more halogen atoms. The term "halogen" means F, Cl, Br or I. Preferably the halogen in a haloalkyl or haloalkoxy is F.

"Hydroxyalkyl" is an alkyl group substituted with hydroxy.

"Alkoxyalkyl" is an alkyl group substituted with alkoxy.

An "alkenyl" means branched or straight-chain monovalent hydrocarbon radical containing at least one double bond. Alkenyl may be mono or polyunsaturated, and may exist in the E or Z configuration. Unless otherwise specified, an alkenyl group typically has 2-6 carbon atoms, i.e. ($C_2$-$C_6$)alkenyl. For example, "($C_2$-$C_6$)alkenyl" means a radical having from 2-6 carbon atoms in a linear or branched arrangement.

"Alkynyl" means branched or straight-chain monovalent hydrocarbon radical containing at least one triple bond. Unless otherwise specified, an alkynyl group typically has 2-6 carbon atoms, i.e. ($C_2$-$C_6$)alkynyl. For example, "($C_2$-$C_6$)alkynyl" means a radical having from 2-6 carbon atoms in a linear or branched arrangement.

"Cycloalkyl" means a saturated aliphatic cyclic hydrocarbon radical, typically containing from 3-8 ring carbon atoms, i.e., ($C_3$-$C_8$)cycloalkyl. ($C_3$-$C_8$)cycloalkyl includes, but is not limited to, cyclopropyl, cyclobutyl, cyclopentyl, cyclohexyl, cycloheptyl and cyclooctyl.

"Cycloaliphatic" means $C_3$-$C_{12}$ monocyclic ($C_3$-$C_8$) or multicyclic ($C_7$-$C_{12}$, e.g., bicyclic, tricyclic, spirocyclic, etc.) hydrocarbon that is completely saturated or has one or more unsaturated bonds but is not an aromatic group, i.e., ($C_3$-$C_8$)cycloalkyl or ($C_3$-$C_8$)cycloalkenyl. Examples of a cycloaliphatic group are cyclopropyl, cyclobutyl, cyclopentyl, cyclopentenyl, cyclohexyl and cyclohexenyl.

The term "aryl group" used alone or as part of a larger moiety as in "aralkyl", "aralkoxy", or "aryloxyalkyl", means a carbocyclic aromatic ring. It also includes a phenyl ring fused with a cycloalkyl or cycloaliphatic group. The term "aryl" may be used interchangeably with the terms "aryl ring" "carbocyclic aromatic ring", "aryl group" and "carbocyclic aromatic group". An aryl group typically has six to fourteen ring atoms. Examples includes phenyl, naphthyl, anthracenyl, 1,2-dihydronaphthyl, 1,2,3,4-tetrahydronaphthyl, fluorenyl, indanyl, indenyl and the like. A "substituted aryl group" is substituted at any one or more substitutable ring atom, which is a ring carbon atom bonded to a hydrogen.

The term "heteroaryl", "heteroaromatic", "heteroaryl ring", "heteroaryl group", "heteroaromatic ring", and "heteroaromatic group", are used interchangeably herein. "Heteroaryl" when used alone or as part of a larger moiety as in "heteroaralkyl" or "heteroarylalkoxy", refers to aromatic ring groups having five to fourteen ring atoms selected from carbon and at least one (typically 1 to 4, more typically 1 or 2) heteroatoms (e.g., oxygen, nitrogen or sulfur). "Heteroaryl" includes monocyclic rings and polycyclic rings in which a monocyclic heteroaromatic ring is fused to one or more other aromatic or heteroaromatic rings. As such, "5-14 membered heteroaryl" includes monocyclic, bicyclic or tricyclic ring systems.

Examples of monocyclic 5-6 membered heteroaryl groups include furanyl (e.g., 2-furanyl, 3-furanyl), imidazolyl (e.g., N-imidazolyl, 2-imidazolyl, 4-imidazolyl, 5-imidazolyl), isoxazolyl (e.g., 3-isoxazolyl, 4-isoxazolyl, 5-isoxazolyl), oxadiazolyl (e.g., 1,2,3-oxadiazolyl, 1,2,4-oxadiazolyl, 1,3, 4-oxadiazolyl), oxazolyl (e.g., 2-oxazolyl, 4-oxazolyl, 5-oxazolyl), pyrazolyl (e.g., 3-pyrazolyl, 4-pyrazolyl, 5-pyrazolyl), pyrrolyl (e.g., 1-pyrrolyl, 2-pyrrolyl, 3-pyrrolyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), thiazolyl (e.g., 2-thiazolyl, 4-thiazolyl, 5-thiazolyl), isothiazolyl, triazolyl (e.g., 1,2,3-triazolyl, 1,2,4-triazolyl, 1,3,4-triazolyl), tetrazolyl (e.g., tetrazolyl), and thienyl (e.g., 2-thienyl, 3-thienyl). Examples of polycyclic aromatic heteroaryl groups include carbazolyl, benzimidazolyl, benzothienyl, benzofuranyl, isobenzofuranyl, indolyl, benzotriazolyl, benzothiazolyl, benzoxazolyl, quinolinyl, isoquinolinyl, indazolyl, isoindolyl, acridinyl, or benzisoxazolyl. A "substituted heteroaryl group" is substituted at any one or more substitutable ring atom, which is a ring carbon or ring nitrogen atom bonded to a hydrogen.

"Heterocyclyl" means a saturated or unsaturated non-aromatic 4-12 membered ring radical optionally containing one or more double bonds. It can be monocyclic, bicyclic, tricyclic, spirocyclic, or fused. The heterocycloalkyl contains 1 to 4 heteroatoms, which may be the same or different, selected from N, O or S. The heterocyclyl ring optionally contains one or more double bonds and/or is optionally fused with one or more aromatic rings (e.g., phenyl ring). The term "heterocyclyl" is intended to include all the possible isomeric forms. Examples of heterocycloalkyl include, but are not limited to, azetidinyl, morpholinyl, thiomorpholinyl, pyrrolidinonyl, pyrrolidinyl, piperidinyl, piperazinyl, hydantoinyl, valerolactamyl, oxiranyl, oxetanyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl, and tetrahydrothiopyranyl. Examples of polycyclic heterocycloalkyl groups include dihydroindolyl, dihydroisoindolyl, dihydrobenzimidazolyl, dihydrobenzothienyl, dihydrobenzofuranyl, dihydroisobenzofuranyl, dihydrobenzotriazolyl, dihydrobenzothiazolyl, dihydrobenzoxazolyl, dihydroquinolinyl, tetrahydroquinolinyl, dihydroisoquinolinyl, tetrahydroisoquinolinyl, dihydroindazolyl, dihydroacridinyl, tetrahydroacridinyl, dihydrobenzisoxazolyl, chroman, chromene, isochroman and isochromene.

The term "Spiro" refers to a cycloaliphatic or heterocyclyl that shares one ring carbon atom with another cycloaliphatic or heterocyclyl group in the molecule.

Certain of the compounds described herein may exist in various stereoisomeric or tautomeric forms. Stereoisomers are compounds which differ only in their spatial arrangement. When a disclosed compound is named or depicted by structure without indicating stereochemistry, it is understood that the name or structure encompasses all possible stereoisomers, geometric isomers, including essentially pure stereo or geometric isomers, as well as combination thereof.

When a geometric isomer is depicted by name or structure, it is to be understood that the geometric isomeric purity of the named or depicted geometric isomer is at least 60%, 70%, 80%, 90%, 99% or 99.9% pure by weight. Geometric isomeric purity is determined by dividing the weight of the named or depicted geometric isomer in the mixture by the total weight of all of the geomeric isomers in the mixture.

Enantiomeric and diastereomeric mixtures can be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well-known asymmetric synthetic methods.

When a compound is designated by a name or structure that indicates a single enantiomer, unless indicated otherwise, the compound is at least 60%, 70%, 80%, 90%, 99% or 99.9% optically pure (also referred to as "enantiomerically pure"). Optical purity is the weight in the mixture of the named or depicted enantiomer divided by the total weight in the mixture of both enantiomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

Included in the present teachings are pharmaceutically acceptable salts of the compounds disclosed herein. The disclosed compounds have basic amine groups and therefore can form pharmaceutically acceptable salts with pharmaceutically acceptable acid(s). Suitable pharmaceutically acceptable acid addition salts of the compounds described herein include salts of inorganic acids (such as hydrochloric acid, hydrobromic, phosphoric, metaphosphoric, nitric, and sulfuric acids) and of organic acids (such as, benzenesulfonic, benzoic, citric, ethanesulfonic, gluconic, glycolic, isethionic, lactic, lactobionic, methanesulfonic, succinic, and p-toluenesulfonic). Compounds of the present teachings with acidic groups such as carboxylic acids can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts). Compounds with a quaternary ammonium group also contain a counteranion such as chloride, bromide, iodide, acetate, perchlorate and the like. Other examples of such salts include hydrochlorides, hydrobromides, sulfates, methanesulfonates, nitrates, citrates, or mixtures thereof including racemic mixtures], succinates, benzoates and salts with amino acids such as glutamic acid.

Compounds described herein can inhibit RIPK2. Thus, generally, compounds described herein are useful in the treatment of diseases or conditions associated with such kinases.

In one embodiment, the compounds described herein are RIPK2 inhibitors, and are useful for treating diseases, such as cancer, associated with such kinase(s). Alternatively, the compounds described herein are RIPK2 inhibitors and are useful for treating diseases associated with RIPK2, such as cancers, autoinflammatory diseases or autoimmune diseases.

Another aspect of the present teachings relates to a method of treating a subject with cancer comprising administering to the subject an effective amount of a compound described herein. In one embodiment, the compounds described herein inhibit the growth of a tumor.

Cancers that can be treated (including reduction in the likelihood of recurrence) by the methods of the present teachings include breast cancer, colon cancer, and ovarian cancer. In one embodiment, the cancer is selected from leukemia, acute myeloid leukemia, chronic myelogenous leukemia, breast cancer, brain cancer, colon cancer, colorectal cancer, head and neck cancer, hepatocellular carcinoma, lung adenocarcinoma, metastatic melanoma, pancreatic cancer, prostate cancer, ovarian cancer and renal cancer. In one embodiment, the cancer is lung cancer, colon cancer, brain cancer, neuroblastoma, prostate cancer, melanoma, glioblastoma multiforme or ovarian cancer. In another embodiment, the cancer is lung cancer, breast cancer, colon cancer, brain cancer, neuroblastoma, prostate cancer, melanoma, glioblastoma multiforme or ovarian cancer. In yet another embodiment, the cancer is breast cancer, colon cancer and lung cancer. In another embodiment, the cancer is a breast cancer. In yet another embodiment, the cancer is a basal sub-type breast cancer or a luminal B sub-type breast cancer. In yet another embodiment, the cancer is a basal sub-type breast cancer. In yet another embodiment, the basal sub-type breast cancer is ER (estrogen receptor), HER2 and PR (progesterone receptor) negative breast cancer. In yet another embodiment, the cancer is a soft tissue cancer. A "soft tissue cancer" is an art-recognized term that encompasses tumors derived from any soft tissue of the body. Such soft tissue connects, supports, or surrounds various structures and organs of the body, including, but not limited to, smooth muscle, skeletal muscle, tendons, fibrous tissues, fatty tissue, blood and lymph vessels, perivascular tissue, nerves, mesenchymal cells and synovial tissues. Thus, soft tissue cancers can be of fat tissue, muscle tissue, nerve tissue, joint tissue, blood vessels, lymph vessels, and fibrous tissues. Soft tissue cancers can be benign or malignant. Generally, malignant soft tissue cancers are referred to as sarcomas, or soft tissue sarcomas. There are many types of soft tissue tumors, including lipoma, lipoblastoma, hibernoma, liposarcoma, leiomyoma, leiomyosarcoma, rhabdomyoma, rhabdomyosarcoma, neurofibroma, schwannoma (neurilemoma), neuroma, malignant schwannoma, neurofibrosarcoma, neurogenic sarcoma, nodular tenosynovitis, synovial sarcoma, hemangioma, glomus tumor, hemangiopericytoma, hemangioendothelioma, angiosarcoma, Kaposi sarcoma, lymphangioma, fibroma, elastofibroma, superficial fibromatosis, fibrous histiocytoma, fibrosarcoma, fibromatosis, dermatofibrosarcoma protuberans (DFSP), malignant fibrous histiocytoma (MFH), myxoma, granular cell tumor, malignant mesenchymomas, alveolar soft-part sarcoma, epithelioid sarcoma, clear cell sarcoma, and desmoplastic small cell tumor. In a particular embodiment, the soft tissue cancer is a sarcoma selected from the group consisting of a fibrosarcoma, a gastrointestinal sarcoma, a leiomyosarcoma, a dedifferentiated liposarcoma, a pleomorphic liposarcoma, a malignant fibrous histiocytoma, a round cell sarcoma, and a synovial sarcoma.

Another aspect of the present teachings relates to a method of treating a subject with autoimmune diseases comprising administering to the subject an effective amount of a compound described herein. In one embodiment, the compounds described herein inhibit the growth of a tumor.

The autoimmune diseases include, but not limited to, rheumatoid arthritis (RA), systemic lupus erythematosus (SLE), multiple sclerosis (MS), Crohn's disease, psoriasis and asthma.

Another aspect of the present teachings relates to a method of treating a subject with auto-inflammatory diseases comprising administering to the subject an effective amount of a compound described herein.

The auto-inflammatory diseases include, but not limited to, familial Mediterranean fever (FMF), Tumor Necrosis Factor (TNF) receptor-associated periodic syndrome (TRAPS), mevalonate kinase deficiency/hyperimmunoglobulin D syndrome (MKD/HIDS), Muckle-Wells syndrome (MWS), familial cold autoinflammatory syndrome (FCAS), neonatal-onset multisystem inflammatory disease (NOMID), periodic fever, aphthous stomatitis, pharyngitis and adenitis (PFAPA syndrome), pyogenic sterile arthritis, pyoderma gangrenosum, acne (PAPA), deficiency of the interleukin-1 receptor antagonist (DIRA), Behcet's disease, Majeed Syndrome, Chronic recurrent multifocal osteomyelitis (CRMO), Schnitzler syndrome, and Blau syndrome.

In some embodiments, the present teachings provide methods of treating a subject with a cancer comprising administering to the subject an effective amount of a compound represented by Structural Formula (I) in combination with an effective anti-cancer therapy. In one embodiment, the cancer is a metastatic cancer. A "metastatic cancer" is a cancer that has spread from its primary site to other parts of the body.

The anti-cancer therapy described herein includes administration of an anti-cancer agent. An "anti-cancer agent" is a compound, which when administered in an effective amount to a subject with cancer, can achieve, partially or substantially, one or more of the following: arresting the growth, reducing the extent of a cancer (e.g., reducing size of a tumor), inhibiting the growth rate of a cancer, and ameliorating or improving a clinical symptom or indicator associated with a cancer (such as tissue or serum components) or increasing longevity of the subject.

The anti-cancer agents suitable for use in the methods described herein include any anti-cancer agents that have been approved for the treatment of cancer. In one embodiment, the anti-cancer agent includes, but is not limited to, a targeted antibody, an angiogenesis inhibitor, an alkylating agent, an antimetabolite, a vinca alkaloid, a taxane, a podophyllotoxin, a topoisomerase inhibitor, a hormonal antineoplastic agent and other antineoplastic agents.

In one embodiment, the anti-cancer agents that can be used in methods described herein include, but are not limited to, paclitaxel, docetaxel, 5-fluorouracil, trastuzumab, lapatinib, bevacizumab, letrozole, goserelin, tamoxifen, cetuximab, panitumumab, gemcitabine, capecitabine, irinotecan, oxaliplatin, carboplatin, cisplatin, doxorubicin, epirubicin, cyclophosphamide, methotrexate, vinblastine, vincristine, melphalan, cytarabine, etoposide, daunorubicin, bleomycin, mitomycin and adriamycin and a combination thereof.

In one embodiment, the anti-cancer agent and the compound represented by Structural Formula (I) are administered contemporaneously. When administered contemporaneously, the anti-cancer agent and the compound can be administered in the same formulation or in different formulations. Alternatively, the compound and the additional anti-cancer agent are administered separately at different times.

The term an "effective amount" means an amount when administered to the subject which results in beneficial or desired results, including clinical results, e.g., inhibits, suppresses or reduces the cancer (e.g., as determined by clinical symptoms or the amount of cancer cells) in a subject as compared to a control.

As used herein, "treating a subject with a cancer" includes achieving, partially or substantially, one or more of the following: arresting the growth, reducing the extent of the cancer (e.g., reducing size of a tumor), inhibiting the growth rate of the cancer, ameliorating or improving a clinical symptom or indicator associated with the cancer (such as tissue or serum components) or increasing longevity of the subject; and reducing the likelihood of recurrence of the cancer.

Generally, an effective amount of a compound taught herein varies depending upon various factors, such as the given drug or compound, the pharmaceutical formulation, the route of administration, the type of disease or disorder, the identity of the subject or host being treated, and the like, but can nevertheless be routinely determined by one skilled in the art. An effective amount of a compound of the present teachings may be readily determined by one of ordinary skill by routine methods known in the art.

In an embodiment, an effective amount of a compound taught herein ranges from about 0.1 to about 1000 mg/kg body weight, alternatively about 1 to about 500 mg/kg body weight, and in another alternative, from about 20 to about 300 mg/kg body weight. In another embodiment, an effective amount of a compound taught herein ranges from about 0.5 to about 5000 mg/m$^2$, alternatively about from 5 to about 2500 mg/m$^2$, and in another alternative from about 50 to about 1000 mg/m$^2$. The skilled artisan will appreciate that certain factors may influence the dosage required to effectively treat a subject suffering from cancer or reduce the likelihood of recurrence of a cancer. These factors include, but are not limited to, the severity of the disease or disorder, previous treatments, the general health and/or age of the subject and other diseases present.

Moreover, for methods described herein (including treating a subject with a cancer or reducing the likelihood of recurrence of a cancer), a "treatment" or dosing regimen of a subject with an effective amount of the compound of the present teachings may consist of a single administration, or alternatively comprise a series of applications. For example, the compound of the present teachings may be administered at least once a week. However, in another embodiment, the compound may be administered to the subject from about one time per week to once daily for a given treatment. The length of the treatment period depends on a variety of factors, such as the severity of the disease, the age of the patient, the concentration and the activity of the compounds of the present teachings, or a combination thereof. It will also be appreciated that the effective dosage of the compound used for the treatment may increase or decrease over the course of a particular treatment regime. Changes in dosage may result and become apparent by standard diagnostic assays known in the art. In some instances, chronic administration may be required.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

The compounds taught herein can be administered to a patient in a variety of forms depending on the selected route of administration, as will be understood by those skilled in the art. The compounds of the present teachings may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration can be by continuous infusion over a selected period of time.

The compounds taught herein can be suitably formulated into pharmaceutical compositions for administration to a subject. The pharmaceutical compositions of the present teachings optionally include one or more pharmaceutically acceptable carriers and/or diluents therefor, such as lactose, starch, cellulose and dextrose. Other excipients, such as flavoring agents; sweeteners; and preservatives, such as methyl, ethyl, propyl and butyl parabens, can also be included. More complete listings of suitable excipients can be found in the Handbook of Pharmaceutical Excipients (5$^{th}$ Ed., Pharmaceutical Press (2005)). A person skilled in the art would know how to prepare formulations suitable for various types of administration routes. Conventional procedures and ingredients for the selection and preparation of suitable formulations are described, for example, in Remington's Pharmaceutical Sciences (2003—20th edition) and in The United States Pharmacopeia: The National Formulary (USP 24 NF19) published in 1999. The carriers, diluents and/or excipients are "acceptable" in the sense of being compatible with the other ingredients of the pharmaceutical composition and not deleterious to the recipient thereof.

Typically, for oral therapeutic administration, a compound of the present teachings may be incorporated with excipient and used in the form of ingestible tablets, buccal tablets, troches, capsules, elixirs, suspensions, syrups, wafers, and the like.

Typically for parenteral administration, solutions of a compound of the present teachings can generally be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms.

Typically, for injectable use, sterile aqueous solutions or dispersion of, and sterile powders of, a compound described herein for the extemporaneous preparation of sterile injectable solutions or dispersions are appropriate.

For nasal administration, the compounds of the present teachings can be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

For buccal or sublingual administration, the compounds of the present teachings can be formulated with a carrier such as sugar, acacia, tragacanth, or gelatin and glycerine, as tablets, lozenges or pastilles.

For rectal administration, the compounds described herein can be formulated in the form of suppositories containing a conventional suppository base such as cocoa butter.

The compounds of invention may be prepared by methods known to those skilled in the art, as illustrated by the general schemes and procedures below and by the preparative examples that follow. All starting materials are either commercially available or prepared by methods known to those skilled in the art and the procedures described below.

General synthetic approaches to the 1H-indazole core have been reviewed in literature (Schmidt A. et al. *Eur. J. Org. Chem.* 2008, 4073-4095).

In one approach, the 5H-pyrrolo[3,2-d]pyrimidine ring can be activated through a deportation followed by electrophilic quenching effectively introducing halogens (e.g. Br, I) or metals (e.g. SnR$_3$, B(OR)$_2$) (Scheme 1) appropriate to undergo cross-coupling reactions as exemplified by Suzuki-Miyarua cross coupling that also cleaves the aryl arylsulfonamide group. The final amination can be facilitated by a suitable metal catalyst with or without an introduction of the additional protecting group. The same transformation can be achieved under a S$_N$Ar reaction at high temperatures.

Scheme 1. Deprotonation-electrophilic activation for C-N coupling reactions

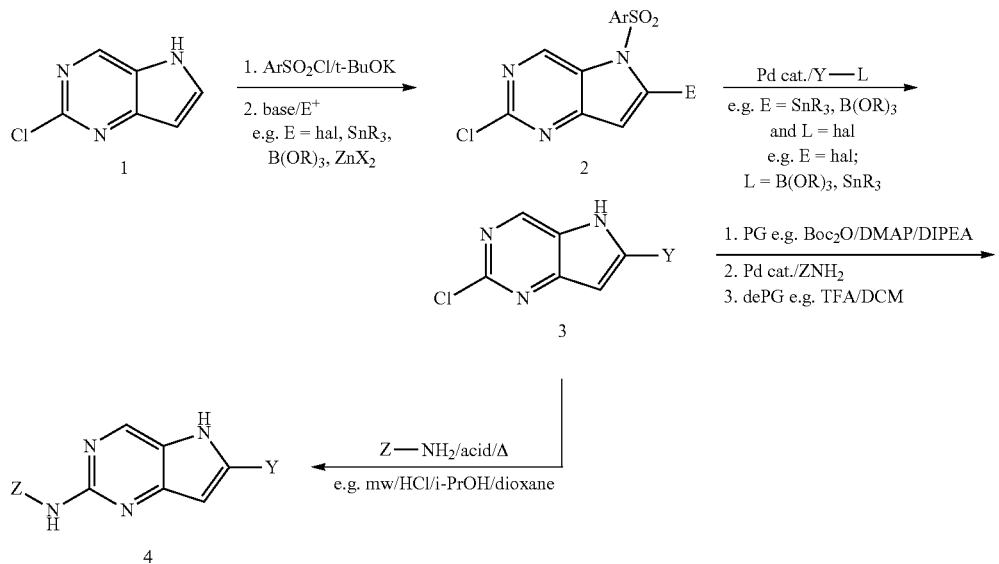

In another approach, the ring can be synthesized in a sequence initiated by a Sonogashira reaction followed by a base induced ring closure of intermediate 9 (Scheme 2). Commercially available pyrimidine 8 can be also be synthesized in a number of approaches presented in Scheme by introduction of the missing functionalities through amination of 6 or halogenation of 7.

EXEMPLIFICATION

Example A: Synthesis

General Methods

Commercially available starting materials, reagents, and solvents were used as received. In general, anhydrous reactions were performed under an inert atmosphere such as Scheme 2. Sonogashire Coupling and C-N coupling reactions.

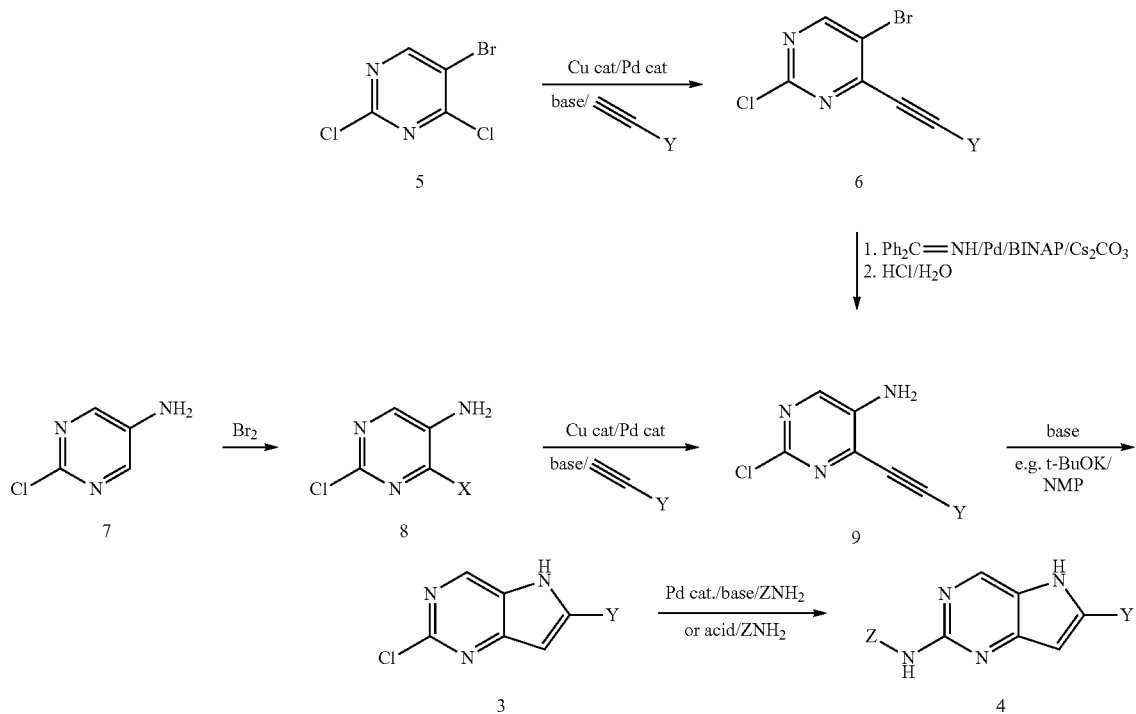

nitrogen or Argon. PoraPak® Rxn CX refers to a commercial cation-exchange resin available from Waters.

Microwave reactions were performed with a Biotage Initiator microwave reactor. Reaction progress was generally monitored by TLC using Merck silica gel plates with visualization by UV at 254 nm, by analytical HPLC or by LCMS (Bruker Exquire 4000). Flash column chromatographic purification of intermediates or final products was performed using 230-400 mesh silica gel 60 from EMD chemicals or Silicycle, or purified using a Biotage Isolera with KP-SIL or HP-SIL silica cartridges, or KP-NH basic modified silica and corresponding samplets. Reverse-phase HPLC purification was performed on a Varian PrepStar model SD-1 HPLC system with a Varian Monochrom 10u C-18 reverse-phase column using a of about 5-30 MeCN or MeOH/0.05 TFA-H$_2$O to 70-90% MeCN or MeOH/0.05% TFA-H$_2$O over a 20-40-min period at a flow rate of 30-50 mL/min Reverse phase purification was also performed using a Biotage Isolera equipped with a KP-C$_{18}$-HS column using a gradient between 5-95% MeOH (or MeCN)/0.1% TFA in H$_2$O. Proton NMRs were recorded on a Bruker 400 MHz spectrometer, and mass spectra were obtained using a Bruker Esquire 4000 spectrometer.

Compound names were generated using the software built into CambridgeSoft-PerkinElmer's ChemBioDraw Ultra version 11.0 or 12.0.

Abbreviations

Ac Acetyl
aq aqueous
anh anhydrous
Ar argon (in the experimental part); aromatic/heteroaromatic group in schemes
BINAP 2,2'-bis(diphenylphosphino)-1,1'-binaphthyl
Boc tert-butoxycarbonyl
br. broad
calcd calculated
d doublet (only when used within 1H NMR spectra)
d day
DCM dichloromethane
DIPEA diisopropylethylamine
DMF N,N-dimethylformamide
DMSO dimethylsulfoxide
dppf 1,1'-bis(diphenylphosphino)ferrocene
h hour
hal halogen
HPLC high performance liquid chromatography
I.P. Intraperitoneal injection
LC-MS liquid chromatography coupled to mass spectrometry
LDA lithium diisopropylamide
min minute
m multiplet
mw microwave irradiation
MS ESI mass spectra, electrospray ionization
ND not determined
NMP 1-methyl-2-pyrrolidone
NMR nuclear magnetic resonance
O/N overnight
pin pinacol
prep preparative
p.o. oral administration
Q.D. dosed once a day
Q.W. dosed once weekly
rt room temperature
RP reverse phase
s singlet
satd saturated
SMs starting materials
S$_N$Ar Nucleophilic Aromatic Substitution
SPE solid phase extraction
t triplet
TBTU O-(benzotriazol-1-yl)-N,N,N',N"-tetramethyluronium tetrafluoroborate
temp. temperature
TFA trifluoroacetic acid
TLC thin layer chromatography
THF tetrahydrofuran
xs excess
Xantphos 4,5-bis(diphenylphosphino)-9,9-dimethylxanthene Preparation of Starting Materials General Method A (Sonogashira Coupling, Preparation of 2-Chloro-4-(Ar/Alkylethynyl)Pyrimidin-5-Amine)

Halopyrimidine (1.0 equiv), acetylene (1 equiv) in Et$_3$N (0.9 M) or in Et$_3$N/DMF (1:1 v/v, 0.8 M) were degassed with Ar, charged with CuI (0.1-0.2 euiv) and Pd(PPh$_3$)$_2$Cl$_2$ (0.03 equiv) or Pd(PPh$_3$)$_4$ (0.07 equiv) and heated sealed at 100° C. until completion. The reaction was cooled to rt, filtered or alternatively concentrated under reduced pressure and subjected to aqueous workup before purification by trituration or flash chromatography.

General Method B (t-BuOK-Induced Cyclization)

A solution of 2-chloro-4-(aryl(alkyl)ethynyl)pyrimidin-5-amine in anh NMP (0.25 M) was treated with t-BuOK (2 equiv) added in one portion at rt (exothermic). The reaction was stirred briefly at rt and then at 50° C. for 0.5-1 h. Later, the reaction was cooled to rt and diluted with H$_2$O. The product was collected by filtration and rinsing with H$_2$O.

General Method C (Buchwald-Hartwig Pd-Catalyzed Amination)

A dry vial was charged with 2-chloro-5H-pyrrolo[3,2-d]pyrimidine or tert-butyl 2-chloro-5H-pyrrolo[3,2-d]pyrimidine-5-carboxylate (1 equiv), K$_2$CO$_3$ (10 equiv), ArNH$_2$ (1.8 equiv) and Pd(OAc)$_2$ (0.1 equiv)_ in ahn dioxane (0.07 M). The reaction mixture was degassed with Ar and charged with Xantphos (0.2 mmol). The reaction vial was sealed, degassing was repeated and the reaction was stirred briefly at rt then in an oil bath at 100° C. overnight. Typically the reaction mixture was cooled to rt, filtered using DCM and MeOH to transfer and rinse. The filtrate was concentrated under reduced pressure, purified by flash chromatography (EtOAc in DCM or MeOH in DCM). In the case of Boc protected material (some loss of Boc was observed in the first step), the material was taken into DCM/TFA (5:1 v/v) and stirred at rt for 1 h. The reaction was then concentrated under reduced pressure and purified by flash chromatography or/and RP HPLC.

General Method D (Acid Catalyzed Amination)

To a solution of 2-chloro-6-(o-tolyl)-5H-pyrrolo[3,2-d]pyrimidine in i-PrOH was added amine or aniline (4-6 equiv) and HCl in dioxane (4 M, 2 equiv). Alternatively an HCl salt of an amine (4-6 equiv) and DIPEA (2-4 equiv) were used. Sealed vial was subjected to microwave irradiation at 170° C. for 2-8 h in a microwave reactor (high pressure: >10 bar). The reaction mixture was purified by reverse phase chromatography.

General Method E (Suzuki-Miyaura Coupling)

To a degassed mixture of dioxane (49 mL) and H$_2$O (12 mL), 2-chloro-6-iodo-5-(phenylsulfonyl)-5H-pyrrolo[3,2-d]pyrimidine (0.744 g, 1.8 mmol), o-tolylboronic acid (0.264 g, 1.9 mmol), K$_2$CO$_3$ (1.01 g, 7.3 mmol) was added Pd(dppf)Cl$_2$·DCM (0.145 g, 0.18 mmol). Degassing was repeated and the reaction was heated in an oil bath under Ar at 105° C. overnight. The reaction then was cooled, concentrated under reduced pressure and purified by flash chromatography (EtOAc-DCM ~10%)

General Method F (Protection with Boc Group)

5H-pyrrolo[3,2-d]pyrimidine, Boc$_2$O (2-4 equiv), DMAP (0.2-0.4 equiv) and DIPEA (1.5 equiv) were stirred in EtOAc at rt overnight. The reaction was then concentrated under reduced pressure and purified by flash chromatography.

Intermediates

Synthesis of
2-(4-(3-aminophenyl)piperazin-1-yl)ethanol

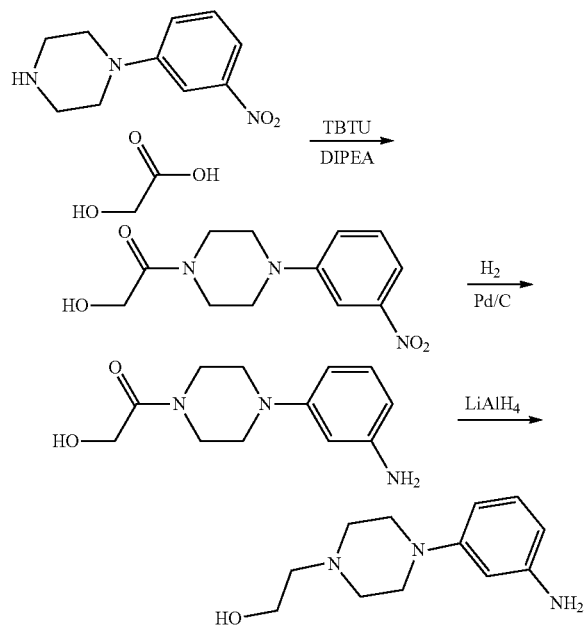

A. 2-hydroxy-1-(4-(3-nitrophenyl)piperazin-1-yl)ethanone

An anh DMF (10 mL) solution of 1-(3-nitrophenyl)piperazine (0.67 g, 3.2 mmol), 2-hydroxyacetic acid (0.261 g, 3.4 mmol), DIPEA (1.2 mL, 6.9 mmol) was treated with TBTU (1.10 g, 3.4 mmol) added in one portion at rt. The reaction was stirred at rt for 2 h, diluted with xs H$_2$O and ice and filtered to afford 2-hydroxy-1-(4-(3-nitrophenyl)piperazin-1-yl)ethanone as a yellow solid (0.546 g, 64%). $^1$H NMR (400 MHz, DMSO-d$_6$) δ ppm 7.66 (t, J=2.10 Hz, 1H), 7.60 (d, J=7.78 Hz, 1H), 7.48 (t, J=8.20 Hz, 1H), 7.40 (dd, J=8.30, 2.10 Hz, 1H), 4.69 (t, J=5.50 Hz, 1H), 4.13 (d, J=5.50 Hz, 2H), 3.56-3.66 (m, 4H), 3.23-3.32 (m, 4H); MS ESI [M+H]$^+$ 266.2 cald for [C$_{12}$H$_{15}$N$_3$O$_4$+H]$^+$ 266.11.

B. 1-(4-(3-aminophenyl)piperazin-1-yl)-2-hydroxyethanone

2-Hydroxy-1-(4-(3-nitrophenyl)piperazin-1-yl)ethanone (0.546 g, 2.06 mmol) and Pd/C (224 mg, 0.2 mmol) were stirred in MeOH (200 mL) under H$_2$ (1 atm) at rt 1 d. The reaction was filtered through Celite, rinsing the reaction flask and the filtration pad with MeOH. Concentration under reduced pressure provided 1-(4-(3-aminophenyl)piperazin-1-yl)-2-hydroxyethanone as a white solid (0.404 g, 83%).). $^1$H NMR (400 MHz, CD$_3$OD) δ ppm 7.00 (t, J=8.00 Hz, 1H), 6.39 (s, 1H), 6.37 (d, J=8.00 Hz, 1H), 6.30 (d, J=8.00 Hz, 1H), 4.27 (s, 2H), 3.68-3.79 (m, 2H), 3.49-3.58 (m, 2H), 3.12 (d, J=4.77 Hz, 4H); MS ESI [M+H]$^+$ 236.2 cald for [C$_{12}$H$_{17}$N$_3$O$_2$+H]$^+$ 235.28.

C. 2-(4-(3-Aminophenyl)piperazin-1-yl)ethanol

An anh THF (24 mL) solution of 1-(4-(3-aminophenyl)piperazin-1-yl)-2-hydroxyethanone (0.404 g, 1.72 mmol) under Ar was treated with LiAlH$_4$ (1.0 M in THF, 6.9 mL, 6.9 mmol) added dropwise at 0° C. After additional 5 min, the cooling bath was removed and the reaction was allowed to warm to rt and then heated at reflux overnight. The reaction mixture was then cooled to rt and poured carefully (dropwise) to a stirred suspension of xs Na$_2$SO$_4$·10H$_2$O in DCM at 0° C. Later the reaction was stirred for 30 min at rt and filtered to afford 2-(4-(3-aminophenyl)piperazin-1-yl)ethanol as a light tan gum that was used without further purification (0.52 g). $^1$H NMR (400 MHz, CD$_3$OD) δ ppm 6.99 (t, J=8.03 Hz, 1H), 6.40 (s, 1H), 6.37 (d, J=8.03 Hz, 1H), 6.29 (d, J=8.03 Hz, 1H), 3.73 (t, J=6.00 Hz, 2H), 3.12-3.19 (m, 4H), 3.04-3.11 (m, 2H), 2.93-2.98 (m, 2H), 2.59 (t, J=6.00 Hz, 2H); MS ESI [M+H]$^+$ 222.2 cald for [C$_{12}$H$_{19}$N$_3$O+H]$^+$ 222.15.

Synthesis of
2-chloro-4-(phenylethynyl)pyrimidin-5-amine

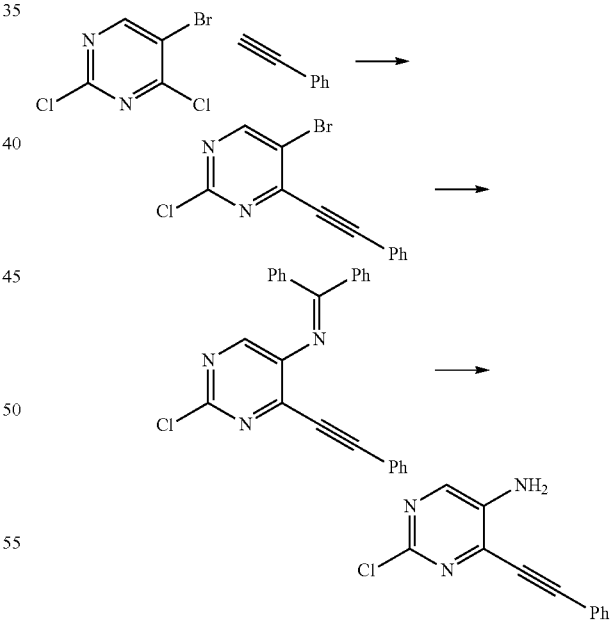

A. -Chloro-N-(diphenylmethylene)-4-(phenylethynyl)pyrimidin-5-amine

5-Bromo-2-chloro-4-(phenylethynyl)pyrimidine (WO2013/078254 p. 166) (0.82 g, 2.9 mmol), diphenylmethanimine (0.58 g, 3.2 mmol), Pd(OAc)$_2$ (26 mg, 0.11 mmol) and Cs$_2$CO$_3$ (1.40 g, 4.3 mmol) in anh PhMe (32 mL)

were degassed with Ar before BINAP (108 mg, 0.17 mmol) was added. The reaction was heated sealed in an oil bath at 105° C. for 17 h, cooled to rt, diluted with DCM and filtered through a 2 um frit. Concentration under reduced pressure and purification by flash chromatography (DCM-EtOAc) afforded 2-chloro-N-(diphenylmethylene)-4-(phenylethynyl)pyrimidin-5-amine as an orange gum (0.71 g). MS ESI [M+H]$^+$ 394.2 cald for [C$_{25}$H$_{16}$ClN$_3$+H]$^+$ 394.1.

B. 2-Chloro-4-(phenylethynyl)pyrimidin-5-amine

2-Chloro-N-(diphenylmethylene)-4-(phenylethynyl)pyrimidin-5-amine (0.28 g, 0.71 mmol) was stirred in THF (6 mL) and aq HCl (2.7 M, 1.5 mL) for 23 h at rt. The reaction was taken into EtOAc, washed with satd aq NaHCO$_3$, dried (Na$_2$SO$_4$), concentrated under reduced pressure and purified by flash chromatography (DCM-MeOH) to afford 2-chloro-4-(phenylethynyl)pyrimidin-5-amine (116 mg, 72%) as a light yellow solid. MS ESI [M+H]$^+$ 230.1, cald for [C$_{12}$H$_8$ClN$_3$+H]$^+$ 230.04.

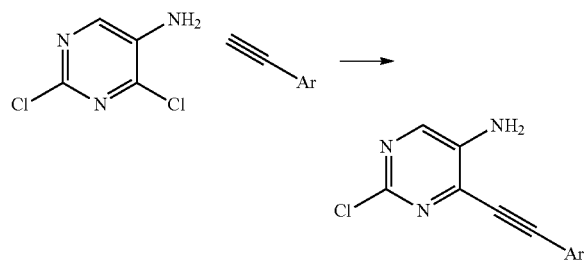

Synthesis of 2-chloro-4-(o-tolylethynyl)pyrimidin-5-amine

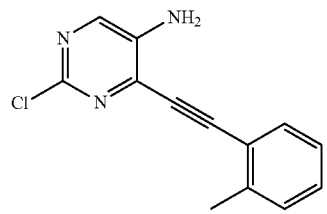 [SMILES: Cc1ccccc1C#Cc1nc(Cl)ncc1N]

A solution of 2,4-dichloropyrimidin-5-amine (4.92 g, 30 mmol), 1-ethynyl-2-methylbenzene (3.63 g, 33 mmol), CuI (0.57 g, 3.0 mmol), Pd(PPh$_3$)$_4$, (3.43 g, 2.1 mmol) in Et$_3$N (20 mL) and DMF (20 mL) was heating in an oil bath at 100° C. for 3 h. H$_2$O and EtOAc were added, the phases were separated and the aqueous layer was extracted with more EtOAc. The combined organic extracts were dried (Na$_2$SO$_4$), filtered and concentrated under reduced pressure. The crude product was triturated with Et$_2$O to give the title compound as a yellow solid (5.92 g, 81%).

TABLE 1

Intermediates synthesized according to General Method A.

| IUPAC name | Structure | MS calcd; MS ESI [M + H]$^+$; | Yield; Appearance; Salt form |
|---|---|---|---|
| 2-chloro-4-((2-chlorophenyl)ethynyl)pyrimidin-5-amine | 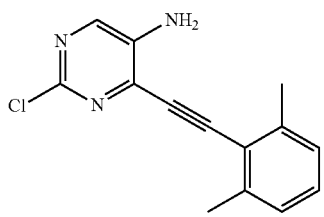 [SMILES: Cc1cccc(C)c1C#Cc1nc(Cl)ncc1N] | [C$_{12}$H$_7$Cl$_2$N$_3$ + H]$^+$ 264.0; 264.1 | 0.64 g (66%) light tan solid; free base |

SMs: 2,4-dichloropyrimidin-5-amine (0.602 g, 3.7 mmol), 1-chloro-2-ethynylbenzene (0.506 g, 3.7 mmol), CuI (0.126 g, 0.66 mmol), Pd(PPh$_3$)$_2$Cl$_2$ (0.130 g, 0.18 mmol), DMF (10 mL), Et$_3$N (10 mL), mw / 100° C. / 2 h
$^1$H NMR (400 MHz, DMSO-d$_6$) δ ppm 8.27 (s, 1 H), 7.91 (d, J = 7.80 Hz, 1 H), 7.63 (d, J = 7.50 Hz, 1 H), 7.52 (t, J = 7.50 Hz, 1 H), 7.45 (t, J = 7.30 Hz, 1 H), 6.14 (brs, 2 H)

| 2-chloro-4-((2,6-dimethylphenyl)ethynyl)pyrimidin-5-amine | | C$_{14}$H$_{12}$ClN$_3$ + H]$^+$ 258.08; 258.2 | 0.173 g (83%); yellow solid; free base |

SMs: 2,4-dichloropyrimidin-5-amine (0.17 g, 0.81 mmol), 2-ethynyl-1,3-dimethylbenzene (0.12 g, 0.89 mmol), CuI (0.015 g, 0.081 mmol), Pd(PPh$_3$)$_4$ (0.14 g, 0.12 mmol)
$^1$H NMR (400 MHz, DMSO-d$_6$) δ ppm 8.22-8.29 (m, 1 H), 7.24-7.31 (m, 1 H), 7.14-7.22 (m, 2 H), 5.93 (br. S, 2 H), 2.44-2.48 (m, 6 H)

TABLE 1-continued

Intermediates synthesized according to General Method A.

| IUPAC name | Structure | MS calcd; MS ESI [M + H]+; | Yield; Appearance; Salt form |
|---|---|---|---|
| 2-chloro-4-(cyclopentylethynyl)pyrimidin-5-amine | 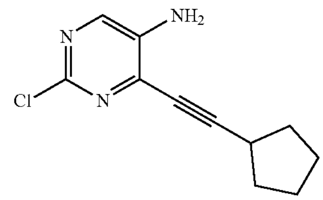 [SMILES: Nc1cnc(Cl)nc1C#CC1CCCC1] | [C$_{11}$H$_{12}$ClN$_3$ + H]+ 222.08; 222.1 | 124 mg (28%); yellow solid; free base |

SMs: 2,4-dichloropyrimidin-5-amine (328 mg, 2.0 mmol), ethynylcyclopentane (207 mg, 2.2 mmol), CuI (38 mg, 0.20 mmol), Pd(PPh$_3$)$_4$ (347 mg, 0.30 mmol)
$^1$H NMR (400 MHz, DMSO-d$_6$) δ ppm 8.13 (s, 1 H), 5.81 (s, 2 H), 2.88-3.02 (m, 1 H), 1.89-2.05 (m, 2 H), 1.62-1.76 (m, 4 H), 1.49-1.61 (m, 2 H)

| 2-chloro-4-(o-tolylethynyl)pyrimidin-5-amine | | [C$_{13}$H$_{10}$ClN$_3$ + H]+ 244.07; 244.1 | 5.92 g (81%); yellow solid; free base |

SMs: 2,4-dichloropyrimidin-5-amine (4.92 g mmol, 30 mmol), 1-ethynyl-2-methylbenzene (3.63 g, 33 mmol).
$^1$H NMR (400 MHz, DMSO-d$_6$) δ ppm 8.24 (s, 1 H), 7.74 (d, J = 7.53 Hz, 1 H), 7.33-7.43 (m, 2 H), 7.24-7.32 (m, 1 H), 6.10 (s, 2 H), 2.48 (s, 3 H)

| 2-chloro-4-(thiophen-3-ylethynyl)pyrimidin-5-amine | | [C$_{10}$H$_6$ClN$_3$S + H]+ 236.01; 236.1 | 146 mg (31%) yellow solid; free base |

SMs: 2,4-dichloropyrimidin-5-amine (328 mg, 2 mmol), 3-ethynylthiophene (238 mg, 2.2 mmol), CuI (38 mg, 0.20 mmol), Pd(PPh$_3$)$_4$ (347 mg, 0.30 mmol)
$^1$H NMR (400 MHz, DMSO-d$_6$) δ ppm 8.20 (s, 1 H), 8.11-8.15 (m, 1 H), 7.64-7.70 (m, 1 H), 7.41 (d, J = 5.02 Hz, 1 H), 6.08-6.18 (m, 2 H)

| 2-chloro-4-((2-fluorophenyl)ethynyl)pyrimidin-5-amine | | [C$_{12}$H$_7$ClFN$_3$ + H]+ 248.04; 248.1 | 562 mg (76%); yellow solid; free base |

SMs: 2,4-dichloropyrimidin-5-amine (492 mg, .03 mmol), ethynyl-2-fluorobenzene (396 mg, 3.3 mmol), CuI (57 mg, 0.30 mmol), Pd(PPh$_3$)$_4$ (520 mg, 0.45 mmol)
$^1$H NMR (400 MHz, DMSO-d$_6$) δ ppm 8.25 (s, 1 H), 7.84-7.91 (m, 1 H), 7.53-7.61 (m, 1 H), 7.29-7.43 (m, 2 H), 6.21 (s, 2 H)

| 2-chloro-4-((tetrahydro-2H-pyran-4-yl)ethynyl)pyrimidin-5-amine | | [C$_{11}$H$_{12}$ClN$_3$O + H]+ 238.08; 238.1 | 610 mg (86%); yellow solid free base |

SMs: 2,4-dichloropyrimidin-5-amine (492 mg, 3 mmol), 4-ethynyltetrahydro-2H-pyran (363 mg, 3.3 mmol), CuI (57 mg, 0.30 mmol), Pd(PPh$_3$)$_4$ (520 mg, 0.45 mmol)

TABLE 1-continued

Intermediates synthesized according to General Method A.

| IUPAC name | Structure | MS calcd; MS ESI [M + H]+ | Yield; Appearance; Salt form |
|---|---|---|---|
| | | | ¹H NMR (400 MHz, CD₃OD) δ ppm 8.14 (s, 1 H), 3.88-3.98 (m, 2 H), 3.51-3.61 (m, 2 H), 3.00-3.09 (m, 1 H), 1.91-2.02 (m, 2 H), 1.75-1.85 (m, 2 H) |
| 2-chloro-4-((2-methoxyphenyl)ethynyl)pyrimidin-5-amine | 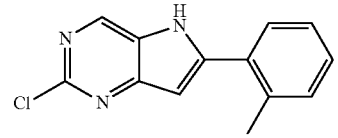 [SMILES: Cc1ccccc1-c1cc2nc(Cl)ncc2[nH]1] | [C₁₃H₁₀ClN₃O + H]⁺ 260.06; 260.2 | 1-81 g (70%); yellow solid; free base |

SMs: 2,4-dichloropyrimidin-5-amine 1.64 g, 10 mmol), ethynyl-2-methoxybenzene (1.45 g, 11 mmol), CuI (198 mg, 1.0 mmol), Pd(PPh₃)₄ (1.16 g, 1.0 mmol)
¹H NMR (400 MHz, CDCl₃) δ ppm 8.16 (s, 1 H), 7.55 (d, J = 7.78 Hz, 1 H), 7.43 (t, J = 7.91 Hz, 1 H), 6.91-7.05 (m, 2 H), 4.61 (br. s., 2 H), 3.95 (s, 3 H)

Synthesis of 2-chloro-6-(o-tolyl)-5H-pyrrolo[3,2-d]pyrimidine by General Method A

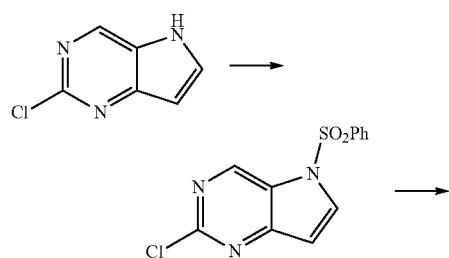

t-BuOK (5.65 g, 50.4 mmol) was added to an NMP (100 mL) solution of 2-chloro-4-(o-tolylethynyl)pyrimidin-5-amine (5.92 g, 24 mmol) at 0° C. The reaction was warmed to rt and stirred for 1 h. The reaction mixture was then cooled to 0° C. and 2 M aq HCl was added to neutralize (pH 7.0). H₂O and EtOAc were added, the phases were separated and the aqueous layer was extracted with EtOAc. The combined organic extracts were dried (Na₂SO₄), filtered and concentrated under reduced pressure. The crude product was triturated with Et₂O and filtered. The filtrate was concentrated under reduced pressure and purified by flash chromatography (100 g SiO₂, 0-40% EtOAc/hexanes) to give a yellow solid that was combined with the product isolated by the filtration (4.46 g, 75%).

Synthesis of 2-chloro-6-(o-tolyl)-5H-pyrrolo[3,2-d]pyrimidine via Suzuki-Miyaura Coupling

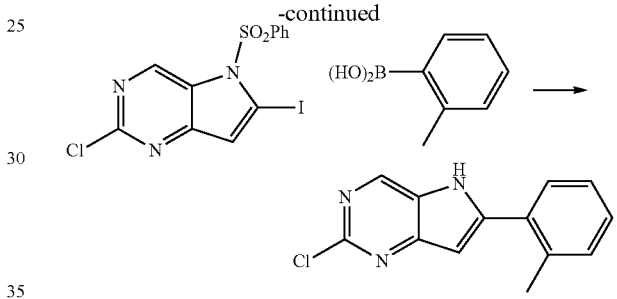

A. 2-Chloro-5-(phenylsulfonyl)-5H-pyrrolo[3,2-d]pyrimidine t-BuOK (0.780 g, 6.9 mmol) was added in four portions to 2-chloro-5H-pyrrolo[3,2-d]pyrimidine (0.861 g, 5.6 mmol) in anh THF (40 mL) with cooling in a H₂O bath. The reaction was stirred for 10 min, PhSO₂Cl was added over 15 min (0.9 mL, 7.0 mmol) and the reaction was left stirring overnight at rt. THF was removed under reduced pressure, the residue was taken into EtOAc, washed with brine (2×) and dried (Na₂SO₄) to afford 2-chloro-5-(phenylsulfonyl)-5H-pyrrolo[3,2-d]pyrimidine as a white solid (1.59 g, 97%) that was used without further purification. ¹H NMR (400 MHz, CDCl₃) δ ppm 9.22 (s, 1H), 7.91-7.99 (m, 3H), 7.65-7.71 (m, 1H), 7.52-7.60 (m, 2H), 6.82 (d, J=3.76 Hz, 1H); MS ESI [M+H]⁺ 294.1, cald for [C₁₂H₈ClN₃O₂S+H]⁺ 294.0.

A. 2-Chloro-6-iodo-5-(phenylsulfonyl)-5H-pyrrolo[3,2-d]pyrimidine

LDA (6.2 mL, 1.0 M in THF, 6.2 mmol) was added dropwise over 8 min to anh THF (95 mL) solution of 2-chloro-5-(phenylsulfonyl)-5H-pyrrolo[3,2-d]pyrimidine (1.59 g, 5.4 mmol) stirred at −78° C. under Ar. The reaction was then stirred at the temperature for 80 min before I₂ (1.58 g, 6.2 mmol in anh THF 4 mL) was added over several minutes via cannula. The stirring with cooling was continued for 3 h, then the cooling bath was removed and after 45 min H₂O (20 mL) was added. The reaction was diluted with DCM (500 mL), washed (brine, 2×), dried (Na₂SO₄) and concentrated under reduced pressure. Purification by flash chromatography (EtOAc-DCM 0-10%) afforded 2-chloro-6-iodo-5-(phenylsulfonyl)-5H-pyrrolo[3,2-d]pyrimidine as a white solid (1.05 g, 46%). MS ESI [M+H]⁺ 419.9, calcd for [C₁₂H₇ClIN₃O₂S+H]⁺ 419.9.

B. 2-chloro-6-(o-tolyl)-5H-pyrrolo[3,2-d]pyrimidine

To a degassed mixture of dioxane (49 mL) and H₂O (12 mL), 2-chloro-6-iodo-5-(phenylsulfonyl)-5H-pyrrolo[3,2-d]pyrimidine (0.744 g, 1.8 mmol), o-tolylboronic acid (0.264 g, 1.9 mmol), K₂CO₃ (1.01 g, 7.3 mmol) was added Pd(dppf)Cl₂·DCM (0.145 g, 0.18 mmol). Degassing was repeated and the reaction was heated in an oil bath under Ar at 105° C. overnight. The reaction then was cooled, concentrated under reduced pressure and purified by flash chromatography (EtOAc-DCM 0-10%) to afford 2-chloro-6-(o-tolyl)-5H-pyrrolo[3,2-d]pyrimidine as a white solid (0.32 g, 74%). ¹H NMR (400 MHz, CD₃OD) δ ppm 8.72 (s, 1H), 7.55 (d, J=7.28 Hz, 1H), 7.32-7.43 (m, 3H), 6.69 (s, 1H), 2.49 (s, 3H); MS ESI [M+H]⁺ 244.1, calcd for [C₁₃H₁₀ClN₃+H]⁺ 244.06.

TABLE 2

The following intermediates were synthesized according to General Method B:

| IUPAC name | Structure | MS calcd; MS ESI [M + H]⁺; | Yield; Appearance; Salt form |
|---|---|---|---|
| 2-chloro-6-(2-chlorophenyl)-5H-pyrrolo[3,2-d]pyrimidine | 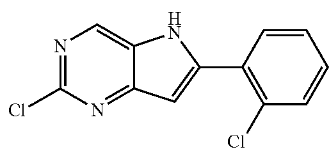 [SMILES: Clc1ncc2[nH]c(-c3ccccc3Cl)cc2n1] | [C₁₂H₇Cl₂N₃ + H]⁺ 264.0; 264.1 | 0.193 g (97%); light tan solid; free base |

SMs: 2-chloro-4-((2-chlorophenyl)ethynyl)pyrimidin-5-amine (198 mg, 0.75 mmol), NMP (3 mL), t-BuOK (188 mg, 1.7 mmol)
¹H NMR (400 MHz, CD₃OD) δ ppm 8.78 (s, 1 H), 7.71-7.77 (m, 1 H), 7.61-7.67 (m, 1 H), 7.48-7.54 (m, 2 H), 6.93 (s, 1 H)

| 2-chloro-6-(o-tolyl)-5H-pyrrolo[3,2-d]pyrimidine | | [C₁₃H₁₀ClN₃ + H]⁺ 244.06; 244.2 | 4.46 g (75%); a yellow solid; free base |

SMs: 2-chloro-4-(o-tolylethynyl)pyrimidin-5-amine (5.92 g, 24 mmol)
¹H NMR (400 MHz, DMSO-d₆) δ ppm 12.32 (br. s., 1 H), 8.78 (s, 1 H), 7.57 (d, J = 7.03 Hz, 1 H), 7.31-7.46 (m, 3 H), 6.73-6.81 (m, 1 H), 2.45 (s, 3 H)

| 2-chloro-6-(2,6-dimethylphenyl)-5H-pyrrolo[3,2-d]pyrimidine | | [C₁₄H₁₂ClN₃ + H]⁺ 258.09; 258.2 | 94 mg (56%) yellow solid; free base |

SMs: 2-chloro-4-((2,6-dimethylphenyl)ethynyl)pyrimidin-5-amine (168 mg, 0.65 mmol), t-BuOK (219 mg, 2.0 mmol)
¹H NMR (400 MHz, DMSO-d₆) δ ppm 12.26 (br. s., 1 H), 8.76 (s, 1 H), 7.26-7.35 (m, 1 H), 7.15-7.23 (m, 2 H), 6.56 (s, 1 H), 2.08 (s, 6 H)

| 2-chloro-6-cyclopentyl-5H-pyrrolo[3,2-6]pyrimidine | | [C₁₁H₁₂ClN₃ + H]⁺ 222.08; 222.2 | 82 mg (66%) yellow solid; free base |

SMs: 2-chloro-4-(cyclopentylethynyl)pyrimidin-5-amine (124 mg, 0.56 mmol), t-BuOK (157 mg, 1.4 mmol)
¹H NMR (400 MHz, DMSO-d₆) δ ppm 11.96 (br. s., 1 H), 8.63 (s, 1 H), 6.38 (s, 1 H), 2.02-2.22 (m, 3 H), 1.84-1.95 (m, 1 H), 1.62-1.81 (m, 5 H)

TABLE 2-continued

The following intermediates were synthesized according to General Method B:

| IUPAC name | Structure | MS calcd; MS ESI [M + H]+ | Yield; Appearance; Salt form |
|---|---|---|---|
| 2-chloro-6-(thiophen-3-yl)-5H-pyrrolo[3,2-d]pyrimidine | 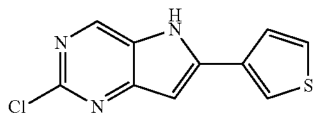 [SMILES: Clc1ncc2[nH]c(-c3ccsc3)cc2n1] | [C₁₀H₆ClN₃S + H]+ 236.01; 236.1 | 128 mg (88%); yellow solid; free base |

SMs: 2-chloro-4-(thiophen-3-ylethynyl)pyrimidin-5-amine (146 mg, 0.62 mmol), t-BuOK (174 mg, 1.6 mmol)
¹H NMR (400 MHz, DMSO-d₆) δ ppm 12.50 (br. s., 1 H), 8.74 (s, 1 H), 8.25 (s, 1 H), 7.76 (s, 2 H), 6.97-7.02 (m, 1 H)

| 2-chloro-6-(2-fluorophenyl)-5H-pyrrolo[3,2-d]pyrimidine | | [C₁₂H₇ClFN₃ + H]+ 248.04; 248.1 | 414 mg (74%); yellow solid; free base |

SMs: 2-chloro-4-((2-fluorophenyl)ethynyl)pyrimidin-5-amine (562 mg, 2.3 mmol), t-BuOK (637 mg, 5.7 mmol)
¹H NMR (400 MHz, CD₃OD) δ ppm 8.76 (s, 1 H), 7.90-7.98 (m, 1 H), 7.61-7.69 (m, 2 H), 7.50-7.60 (m, 1 H), 7.30-7.42 (m, 1 H), 7.02 (s, 1 H)

| 2-chloro-6-(tetrahydro-2H-pyran-4-yl)-5H-pyrrolo[3,2-d]pyrimidine | | [C₁₁H₁₂ClN₃O + H]+ 238.08; 238.1 | 439 mg (72%); yellow solid; free base |

SMs: 2-chloro-4-((tetrahydro-2H-pyran-4-yl)ethynyl)pyrimidin-5-amine (610 mg, 2.6 mmol), t-BuOK (720 mg, 6.4 mmol)
¹H NMR (400 MHz, CD₃OD) δ ppm 8.59 (s, 1 H), 6.41 (s, 1 H), 4.02-4.10 (m, 2 H), 3.60 (s, 2 H), 3.11-3.23 (m, 1 H), 1.94-2.03 (m, 2 H), 1.80-1.94 (m, 2 H)

| 2-chloro-6-(2-methoxyphenyl)-5H-pyrrolo[3,2-d]pyrimidine | | [C₁₃H₁₀ClN₃O + H]+ 260.06; 260.2 | 1.59 g (88%); yellow solid; free base |

SMs: 2-chloro-4-((2-methoxyphenyl)ethynyl)pyrimidin-5-amine (1.81 g, 7.0 mmol), ), t-BuOK (1.96 g, 18 mmol)
¹H NMR (400 MHz, CD₃OD) δ ppm 8.70 (s, 1 H), 7.89 (d, J = 6.78 Hz, 1 H), 7.43-7.52 (m, 1 H), 7.22 (d, J = 8.28 Hz, 1 H), 7.12 (t, J = 7.53 Hz, 1 H), 6.99 (s, 1 H), 4.04 (s, 3 H)

Preparation of Exemplary Compounds of the Invention

Synthesis of N,6-diphenyl-5H-pyrrolo[3,2-d]pyrimidin-2-amine) (Example A1)

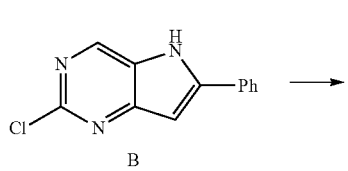

B

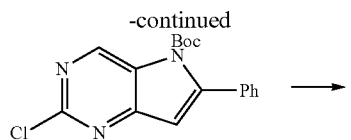

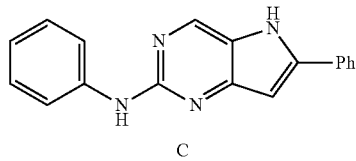

C

A. tert-Butyl 2-chloro-6-phenyl-5H-pyrrolo[3,2-d]pyrimidine-5-carboxylate

2-Chloro-6-phenyl-5H-pyrrolo[3,2-d]pyrimidine (83.8 mg, 0.365 mmol), Boc$_2$O (350 mg, 1.60 mmol), DMAP (29 mg, 0.23 mmol) and DIPEA (0.1 mL, 0.57 mmol) were stirred in EtOAc (24 mL) at rt for 22 h. The reaction was then concentrated under reduced pressure and purified by flash chromatography (0 to 30% EtOAc in DCM) to afford tert-butyl 2-chloro-6-phenyl-5H-pyrrolo[3,2-d]pyrimidine-5-carboxylate as a white solid (0.106 g, 88%). $^1$H NMR (400 MHz, CDCl$_3$) δ ppm 9.31 (s, 1H), 7.41-7.53 (m, 5H), 6.68 (d, J=0.75 Hz, 1H), 1.37 (s, 9H); MS ESI [M+H]$^+$ 330.2, calcd for [C$_{17}$H$_{16}$ClN$_3$O$_2$+H]$^+$ 330.09.

B. N,6-diphenyl-5H-pyrrolo[3,2-d]pyrimidin-2-amine)

A dry vial was charged with tert-butyl 2-chloro-6-phenyl-5H-pyrrolo[3,2-d]pyrimidine-5-carboxylate (62 mg, 0.19 mol), K$_2$CO$_3$ (245 mg, 1.8 mmol), PhNH$_2$ (32 mg, 0.34 mmol) and Pd(OAc)$_2$ (5.6 mg, 0.025 mmol) in ahn dioxane (3 mL). The reaction mixture was degassed with Ar and charged with Xantphos (28.5 mg, 0.049 mmol). The reaction vial was sealed, degassing was repeated and the reaction was stirred briefly at rt then in an oil bath at 100° C. for 22 h. The reaction mixture was cooled to rt, filtered using DCM and MeOH to transfer and rinse. The filtrate was concentrated under reduced pressure and purified by flash chromatography (EtOAc in DCM) to afford crude tert-butyl 2-chloro-6-phenyl-5H-pyrrolo[3,2-d]pyrimidine-5-carboxylate (MS ESI [M+H]$^+$ 387.3, calcd for [C$_{23}$H$_{22}$N$_4$O$_2$+H]$^+$ 387.17) which was taken into DCM/TFA (25 mL, 5:1 v/v) and stirred at rt for 1 h. The reaction was then concentrated under reduced pressure and purified by flash chromatography (EtOAc in DCM 0→60%). Trituration with hexanes then with Et$_2$O-hexanes (1:1 v/v) afforded N,6-diphenyl-5H-pyrrolo[3,2-d]pyrimidin-2-amine as a pale yellow solid (50 mg, 92%). $^1$H NMR (400 MHz, CD$_3$OD) δ ppm 8.70 (s, 1H), 7.95 (d, J=8.30 Hz, 2H), 7.55-7.65 (m, 5H), 7.42-7.49 (m, 2H), 7.26 (t, J=7.50 Hz, 1H), 6.91 (s, 1H); MS ESI [M+H]$^+$ 287.2, calcd for [C$_{18}$H$_{14}$N$_4$+H]$^+$ 287.12.

Synthesis of N-(3-morpholinophenyl)-6-(o-tolyl)-5H-pyrrolo[3,2-d]pyrimidin-2-amine (Example A3)

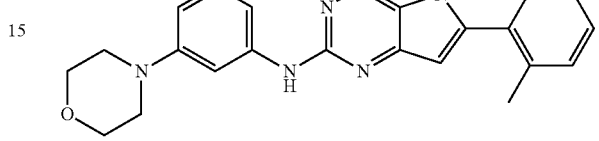

A sealed vial containing 2-chloro-6-(o-tolyl)-5H-pyrrolo[3,2-d]pyrimidine (0.73 g, 3.0 mmol), 3-morpholinoaniline (0.71 g, 4.0 mmol), HCl (4 M in dioxane, 1.5 mL, 6 mmol) in i-PrOH (10 mL) was heated at 170° C. for 2 h in a microwave reactor (high pressure). The reaction mixture was purified by reverse phase chromatography and converted to free base using a PoraPak column. The crude product was dissolved in DCM and precipitated using Et$_2$O to obtain the title compound as a beige solid (593 mg, 51%). The title compound was suspended in DCM (40 mL) and HCl (1 M in Et$_2$O, 5 mL) was added. The solution was sonicated until fully dissolved. The mixture was concentrated in vacuo and triturated with Et$_2$O to give the title compound as a diHCl salt (687 mg, 50%, brown solid).

TABLE 3

The following examples were prepared according to General Methods C or D

| IUPAC name | Structure | Example number MS calcd; MS ESI [M + H]$^+$; HPLC purity at 254 nm | Yield; Appearance; Salt form |
|---|---|---|---|
| N,6-diphenyl-5H-pyrrolo[3,2-d]pyrimidin-2-amine | 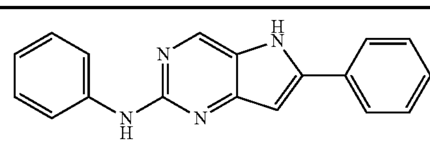 | A1 [C$_{18}$H$_{14}$N$_4$ + H]$^+$ 287.12; 287.2; 99.0% | 0.050 g (92%); a pale yellow solid; free base |

SMs: tert-butyl 2-chloro-6-phenyl-5H-pyrrolo[3,2-d]pyrimidine-5-carboxylate (62 mg, 0.19 mol), K$_2$CO$_3$ (245 mg, 1.8 mmol), PhNH$_2$ (32 mg, 0.34 mmol), Pd(OAc)$_2$ (5.6 mg, 0.025 mmol), dioxane (3 mL), Xantphos (28.5 mg, 0.049 mmol).
$^1$H NMR (400 MHz, CD$_3$OD) δ ppm 8.70 (s, 1 H), 7.95 (d, J = 8.30 Hz, 2 H), 7.55-7.65 (m, 5 H), 7.42-7.49 (m, 2 H), 7.26 (t, J = 7.50 Hz, 1 H), 6.91 (s, 1 H)

| | | | |
|---|---|---|---|
| N-(4-((1-methylpiperidin-4-yl)oxy)phenyl)-6-(o-tolyl)-5H-pyrrolo[3,2-d]pyrimidin-2-amine | | A2; [C$_{25}$H$_{27}$N$_5$O + H]$^+$ 414.22; 414.3; 95.0% | 0.0357 g (53%); pale light solid; free base |

SMs: tert-butyl 2-chloro-6-phenyl-5H-pyrrolo[3,2-d]pyrimidine-5-carboxylate (55.3 mg, 0.16 mol), K$_2$CO$_3$ (221 mg, 1.6 mmol), 4-((1-methylpiperidin-4-yl)oxy)aniline (56.4 mg, 0.27 mmol), Pd(OAc)$_2$ (4.3 mg, 0.019 mmol), dioxane (5 mL), Xantphos (18.5 mg, 0.032 mmol).

TABLE 3-continued

The following examples were prepared according to General Methods C or D

| IUPAC name | Structure | Example number MS calcd; MS ESI [M + H]+; HPLC purity at 254 nm | Yield; Appearance; Salt form |
|---|---|---|---|

¹H NMR (400 MHz, CD₃OD) δ ppm 8.51 (d, J = 1.00 Hz, 1 H), 7.50-7.54 (m, 3 H), 7.29-7.38 (m, 3 H), 6.91-6.95 (m, 2 H), 6.43 (d, J = 0.80 Hz, 1 H), 4.30-4.42 (m, 1 H), 2.69-2.81 (m, 2 H), 2.49 (s, 3 H), 2.35-2.47 (m, 2 H), 2.33 (s, 3 H), 1.94-2.08 (m, 2 H), 1.75-1.92 (m, 2 H)

| N-(3-morpholinophenyl)-6-(o-tolyl)-5H-pyrrolo[3,2-d]pyrimidin-2-amine | | A3; [C₂₃H₂₃N₅O + H]+ 386.19; 386.2; >99% | 0.083 g; (96%); pale yellow solid; free base |

SMs: tert-butyl 2-chloro-6-phenyl-5H-pyrrolo[3,2-d]pyrimidine-5-carboxylate (77.3 mg, 0.22 mol), K₂CO₃ (311 mg, 2.2 mmol), 3-morpholinoaniline (61 mg, 0.34 mmol), Pd(OAc)₂ (6.6 mg, 0.029 mmol), dioxane (5 mL), Xantphos (36 mg, 0.062 mmol).
¹H NMR (400 MHz, CD₃OD) δ ppm 8.75 (s, 1 H), 7.57 (d, J = 7.80 Hz, 1 H), 7.35-7.47 (m, 4 H), 7.20 (s, 1 H), 7.05 (d, J = 8.30 Hz, 1 H), 6.96 (dd, J = 8.50, 2.30 Hz, 1 H), 6.63 (s, 1 H), 3.83-3.90 (m, 4 H), 3.20-3.26 (m, 4 H), 2.51 (s, 3 H).

| N-(3-(4-methylpiperazin-1-yl)phenyl)-6-(o-tolyl)-5H-pyrrolo[3,2-d]pyrimidin-2-amine | | A4; [C₂₄H₂₆N₆ + H]+ 399.22; 399.2; 96.0% | 0.057 g; (53%); yellow solid; TFA salt |

SMs: tert-butyl 2-chloro-6-phenyl-5H-pyrrolo[3,2-d]pyrimidine-5-carboxylate (72.8 mg, 0.21 mol), K₂CO₃ (303 mg, 2.2 mmol), 3-(4-methyl-piperazin-1-yl)aniline (69 mg, 0.36 mmol), Pd(OAc)₂ (5.7 mg, 0.025 mmol), dioxane (5 mL), Xantphos (29.5 mg, 0.051 mmol).
¹H NMR (400 MHz, CD₃OD) δ ppm 8.74 (s, 1 H), 7.58 (d, J = 7.30 Hz, 1 H), 7.30-7.50 (m, 5 H), 7.25 (d, J = 7.80 Hz, 1 H), 6.91 (dd, J = 8.30, 2.30 Hz, 1 H), 6.68 (s, 1 H), 3.85-3.99 (m, 2 H), 3.57-3.70 (m, 2 H), 3.23-3.36 (m, 2 H), 3.07-3.21 (m, 2 H), 2.99 (s, 3 H), 2.52 (s, 3 H).

| 2-(4-(2-methyl-6-((6-(o-tolyl)-5H-pyrrolo[3,2-d]pyrimidin-2-yl)amino)pyrimidin-4-yl)piperazin-1-yl)ethanol | | A5; [C₂₄H₂₈N₈O + H]+ 445.24; 445.3; >99.6% | 0.068 g; (65.0%); pale yellow solid; 2HCl salt |

SMs: tert-butyl 2-chloro-6-phenyl-5H-pyrrolo[3,2-d]pyrimidine-5-carboxylate (72.5 mg, 0.20 mol), K₂CO₃ (280 mg, 2.2 mmol), 2-(4-(6-amino-2-methylpyrimidin-4-yl)piperazin-1-yl)ethanol (82 mg, 0.34 mmol), Pd(OAc)₂ (5.0 mg, 0.022 mmol), dioxane (5 mL), Xantphos (23.5 mg, 0.041 mmol).
¹H NMR (400 MHz, CD₃OD) δ ppm 8.83 (s, 1 H), 7.57 (d, J = 7.30 Hz, 1 H), 7.33-7.46 (m, 2 H), 6.78 (s, 1 H), 6.32 (s, 1 H), 4.62-4.83 (br.m, 2 H), 3.93-4.00 (m, 2 H), 3.76-3.86 (br.m, 2 H), 3.53-3.69 (br.m, 2 H), 3.37-3.43 (m, 2 H), 2.75 (s, 3 H), 2.52 (s, 3 H). 2H obscured by the peaks due to the NMR solvent.

| 6-(2,6-dimethylphenyl)-N-(3-(4-methylpiperazin-1-yl)phenyl)-5H-pyrrolo[3,2-d]pyrimidin-2-amine | | A6; [C₂₅H₂₈N₆ + H]+ 413.25; 413.3; 96.2% | 32 mg, (22%) light brown solid; HCl salt |

SMs: 2-chloro-6-(2,6-dimethylphenyl)-5H-pyrrolo[3,2-d]pyrimidine (82 mg, 0.32 mmol), 3-(4-methylpiperazin-1-yl)aniline (73 mg, 0.38 mmol), Pd(OAc)₂ (11 mg, 0.016 mmol), Xantphos (74 mg, 0.13 mmol), K₂CO₃ (132 mg, 0.96 mmol).
¹H NMR (400 MHz, CD₃OD) δ ppm 8.79 (s, 1 H), 7.35-7.43 (m, 1 H), 7.27-7.35 (m, 2 H), 7.20 (d, J = 7.28 Hz, 2 H), 7.11-7.17 (m, 1 H), 6.94-7.01 (m, 1 H), 6.48 (s, 1 H), 3.83-4.00 (m, 2 H), 3.56-3.69 (m, 2 H), 3.21-3.28 (m, 2 H), 3.08-3.20 (m, 2 H), 2.98 (s, 3 H), 2.18 (s, 6 H)

TABLE 3-continued

The following examples were prepared according to General Methods C or D

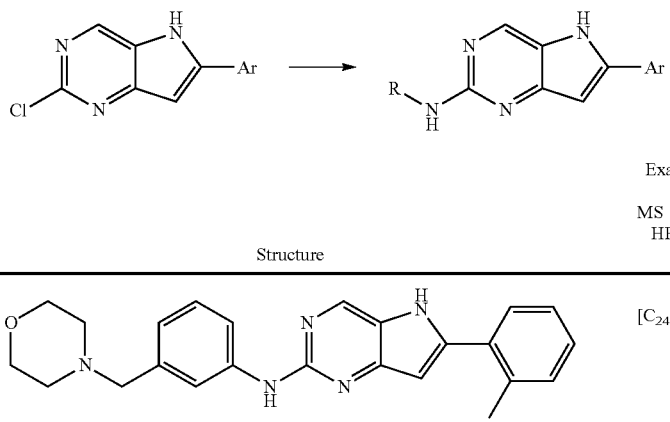

| IUPAC name | Structure | Example number<br>MS calcd;<br>MS ESI [M + H]+;<br>HPLC purity at<br>254 nm | Yield;<br>Appearance;<br>Salt form |
|---|---|---|---|
| N-(3-(morpholinomethyl)phenyl)-6-(o-tolyl)-5H-pyrrolo[3,2-d]pyrimidin-2-amine | 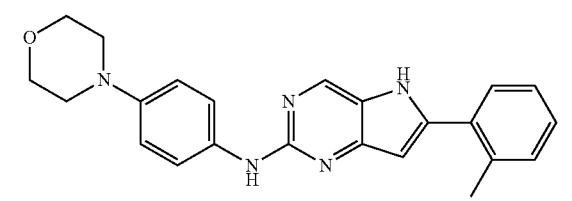 [SMILES: Cc1ccccc1-c1cc2nc(Nc3ccc(N4CCOCC4)cc3)ncc2[nH]1] | A7;<br>[C$_{24}$H$_{25}$N$_5$O + H]+<br>400.21;<br>400.2;<br>99.2% | 0.086 g;<br>(70%);<br>light yellow<br>solid;<br>TFA salt |

SMs: tert-butyl 2-chloro-6-phenyl-5H-pyrrolo[3,2-d]pyrimidine-5-carboxylate (82.6 mg, 0.24 mol), K$_2$CO$_3$ (332 mg, 2.4 mmol), 3-(morpholinomethyl)aniline (76 mg, 0.39 mmol), Pd(OAc)$_2$ (6.1 mg, 0.027 mmol), dioxane (5 mL), Xantphos (32.2 mg, 0.056 mmol).
$^1$H NMR (400 MHz, CD$_3$OD) δ ppm 8.74 (s, 1 H), 7.97 (s, 1 H), 7.83 (d, J = 8.00 Hz, 1 H), 7.58 (d, J = 7.50 Hz, 1 H), 7.53 (t, J = 8.00 Hz, 1 H), 7.36-7.49 (m, 3 H), 7.28 (d, J = 8.00 Hz, 1 H), 6.69 (s, 1 H), 4.42 (s, 2 H), 3.77-4.12 (br.m, 4 H), 3.34-3.44 (br.m, 4 H), 2.53 (s, 3 H).

| N-(4-morpholinophenyl)-6-(o-tolyl)-5H-pyrrolo[3,2-d]pyrimidin-2-amine | 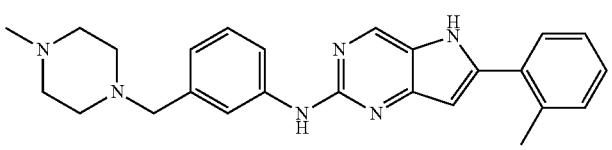 [SMILES: Cc1ccccc1-c1cc2nc(Nc3cccc(CN4CCN(C)CC4)c3)ncc2[nH]1] | A8;<br>[C$_{23}$H$_{23}$N$_5$O + H]+<br>386.19;<br>386.3;<br>97.8% | 0.029 g;<br>(33%);<br>light orange<br>solid;<br>TFA salt |

SMs (method: tert-butyl 2-chloro-6-phenyl-5H-pyrrolo[3,2-d]pyrimidine-5-carboxylate (60.5 mg, 0.18 mol), K$_2$CO$_3$ (243 mg, 1.8 mmol), 4-morpholinoaniline (47 mg, 0.26 mmol), Pd(OAc)$_2$ (4.0 mg, 0.018 mmol), dioxane (5 mL), Xantphos (20.4 mg, 0.035 mmol).
$^1$H NMR (400 MHz, CD$_3$OD) δ ppm 8.73 (s, 1 H), 7.55 (d, J = 7.78 Hz, 1 H), 7.34-7.49 (m, 5 H), 7.14 (d, J = 8.78 Hz, 2 H), 6.58 (s, 1 H), 3.82-3.93 (m, 4 H), 3.18-3.27 (m, 4 H), 2.50 (s, 3 H)

| N-(3-((4-methylpiperazin-1-yl)methyl)phenyl)-6-(o-tolyl)-5H-pyrrolo[3,2-d]pyrimidin-2-amine | 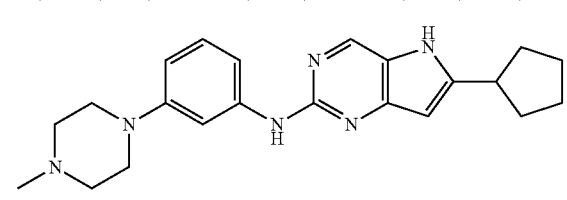 | A9;<br>[C$_{25}$H$_{28}$N$_6$ + H]+<br>413.24;<br>413.3;<br>98.8% | 0.015 g<br>(14%);<br>pale yellow<br>solid;<br>TFA salt |

SMs: tert-butyl 2-chloro-6-phenyl-5H-pyrrolo[3,2-d]pyrimidine-5-carboxylate (70 mg, 0.20 mol), K$_2$CO$_3$ (283 mg, 2.0 mmol), 3-((4-methylpiperazin-1-yl)methyl)aniline*2HCl (85.6 mg, 0.30 mmol), Pd(OAc)$_2$ (11.4 mg, 0.051 mmol), dioxane (5 mL), Xantphos (58.1 mg, 0.10 mmol).
$^1$H NMR (400 MHz, CD$_3$OD) δ ppm 9.10 (s, 1 H), 7.90-7.98 (m, 2 H), 7.85 (d, J = 8.78 Hz, 1 H), 7.59-7.77 (m, 4 H), 7.51 (d, J = 8.28 Hz, 1 H), 6.90 (s, 1 H), 3.91 (s, 2 H), 3.24-3.46 (m, 4 H), 2.81-3.08 (m, 4 H), 2.87 (s, 3 H), 2.47 (s, 3 H).

| 6-cyclopentyl-N-(3-(4-methylpiperazin-1-yl)phenyl)-5H-pyrrolo[3,2-d]pyrimidin-2-amine | 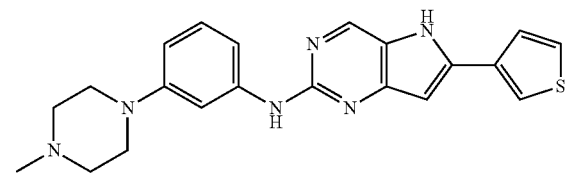 [SMILES: CN1CCN(c2cccc(Nc3ncc4[nH]c(-c5ccsc5)cc4n3)c2)CC1] | A10;<br>[C$_{22}$H$_{28}$N$_6$ + H]+<br>377.25;<br>377.3;<br>96.0% | 10.3 mg (7%);<br>yellow solid;<br>HCl salt |

SMs: 2-chloro-6-cyclopentyl-5H-pyrrolo[3,2-d]pyrimidine (82 mg, 0.37 mmol), 3-(4-methylpiperazin-1-yl)aniline (85 mg, 0.44 mmol), Pd(OAc)$_2$ (12.5 mg, 0.019 mmol), Xantphos (86 mg, 0.15 mmol), K$_2$CO$_3$ (153 mg, 1.1 mmol).
$^1$H NMR (400 MHz, CD$_3$OD) δ ppm 8.58 (s, 1 H), 7.31-7.42 (m, 1 H), 7.27 (br. s., 1 H), 7.06-7.15 (m, 1 H), 6.91-6.98 (m, 1 H), 6.38 (s, 1 H), 3.84-3.95 (m, 2 H), 3.56-3.69 (m, 2 H), 3.23-3.30 (m, 2 H), 3.03-3.17 (m, 2 H), 2.98 (s, 3 H), 2.13-2.30 (m, 3 H), 1.70-1.93 (m, 6 H)

| N-(3-(4-methylpiperazin-1-yl)phenyl)-6-(thiophen-3-yl)-5H-pyrrolo[3,2-d]pyrimidin-2-amine | | A11;<br>[C$_{21}$H$_{22}$N$_6$S + H]+<br>391.16;<br>391.2;<br>98.7% | 43 mg (19%);<br>orange solid;<br>HCl salt |

SMs: 2-chloro-6-(thiophen-3-yl)-5H-pyrrolo[3,2-d]pyrimidine (128 mg, 0.54 mmol), 3-(4-methylpiperazin-1-yl)aniline (125 mg, 0.65 mmol), Pd(OAc)$_2$ (18 mg, 0.027), Xantphos (125 mg, 0.22 mmol), K$_2$CO$_3$ (224 mg, 1.6 mmol)

TABLE 3-continued

The following examples were prepared according to General Methods C or D

| IUPAC name | Structure | Example number MS calcd; MS ESI [M + H]+; HPLC purity at 254 nm | Yield; Appearance; Salt form |
|---|---|---|---|

¹H NMR (400 MHz, CD₃OD) δ ppm 8.65 (s, 1 H), 8.19-8.24 (m, 1 H), 7.65-7.71 (m, 2 H), 7.35-7.41 (m, 1 H), 7.26-7.31 (m, 1 H), 7.13 (d, J = 9.03 Hz, 1 H), 6.96 (d, J = 9.29 Hz, 1 H), 6.84 (s, 1 H), 3.87-3.97 (m, 2 H), 3.60-3.68 (m, 2 H), 3.25-3.30 (m, 2 H), 3.08-3.20 (m, 2 H) 2.98 (s, 3 H)

| 6-(2,6-dimethylphenyl)-N-(3-morpholinophenyl)-5H-pyrrolo[3,2-d]pyrimidin-2-amine | | A12; [C₂₄H₂₅N₅O + H]⁺ 400.22; 400.3; 99.9% | 38 mg (9%); light orange solid; HCl salt |

SMs: 2-chloro-6-(2,6-dimethylphenyl)-5H-pyrrolo[3,2-d]pyrimidine (92 mg, 0.36 mmol), 3-morpholinoaniline (76 mg, 0.43 mmol), Pd(OAc)₂ (8 mg, 0.036 mmol), Xantphos (83 mg, 0.14 mmol), K₂CO₃ (149 mg, 1.1 mmol)

¹H NMR (400 MHz, CD₃OD) δ ppm 8.83 (s, 1 H), 7.91-7.98 (m, 1 H) 7.53-7.60 (m, 1 H), 7.45-7.51 (m, 1 H), 7.28-7.37 (m, 2 H), 7.17-7.25 (m, 2 H), 6.53-6.59 (m, 1 H), 3.99-4.09 (m, 4 H), 3.52-3.64 (m, 4 H), 2.19 (s, 6 H)

| 6-(2-fluorophenyl)-N-(3-morpholinophenyl)-5H-pyrrolo[3,2-d]pyrimidin-2-amine | | A13; [C₂₂H₂₀FN₅O + H]⁺ 390.18; 390.3; 97.4% | 47 mg (11%); yellow solid; HCl salt |

SMs: 2-chloro-6-(2-fluorophenyl)-5H-pyrrolo[3,2-d]pyrimidine (247 mg, 1.0 mmol), 3-morpholinoaniline (214 mg, 1.2 mmol), Pd(OAc)₂ (22 mg, 0.10 mmol), Xantphos (231 mg, 0.40 mmol), K₂CO₃ (414 mg, 3.0 mmol)

¹H NMR (400 MHz, CD₃OD) δ ppm 8.82 (s, 1 H), 7.94-8.00 (m, 1 H), 7.72-7.78 (m, 1 H), 7.58-7.66 (m, 1 H), 7.49-7.56 (m, 1 H), 7.33-7.46 (m, 3 H), 7.22-7.28 (m, 1 H), 7.01 (s, 1 H), 3.96-4.03 (m, 4 H), 3.46-3.55 (m, 4 H)

| N-(3-morpholinophenyl)-6-(tetrahydro-2H-pyran-4-yl)-5H-pyrrolo[3,2-d]pyrimidin-2-amine | | A14; [C₂₁H₂₅N₅O₂ + H]⁺ 380.21; 380.3; >99.8% | 52 mg (10%); beige solid; HCl salt |

SMs: 2-chloro-6-(tetrahydro-2H-pyran-4-yl)-5H-pyrrolo[3,2-d]pyrimidine (300 mg, 1.3 mmol), 3-morpholinoaniline 270 mg, 1.5 mmol), Pd(OAc)₂ (28 mg, 0.13 mmol), Xantphos (147 mg, 0.25 mmol), K₂CO₃ (526 mg, 3.8 mmol)

¹H NMR (400 MHz, CD₃OD) δ ppm 8.69 (s, 1 H), 7.95-8.04 (m, 1 H), 7.46-7.61 (m, 2 H), 7.30-7.39 (m, 1 H), 6.51 (s, 1 H), 4.06 (br. s., 6 H), 3.61 (br. s., 6 H), 3.19-3.27 (m, 1 H), 1.95-2.05 (m, 2 H), 1.82-1.95 (m, 2 H)

| N-(4-(morpholinomethyl)phenyl)-6-(o-tolyl)-5H-pyrrolo[3,2-d]pyrimidin-2-amine | | A15; [C₂₄H₂₅N₅O + H]⁺ 399.21; 400.22; 400.3; >99.8% | 78 mg (18%); orange solid; HCl salt |

SMs: 2-chloro-6-(o-tolyl)-5H-pyrrolo[3,2-d]pyrimidine (243 mg, 1.0 mmol), 4-(morpholinomethyl)aniline (230 mg, 1.2 mmol), Pd(OAc)₂ (22.4 mg, 0.10 mmol), Xantphos (116 mg, 0.20 mmol), K₂CO₃ (414 mg, 3.0 mmol)

¹H NMR (400 MHz, CD₃OD) δ ppm 8.80 (s, 1 H), 7.96 (br. s., 1 H), 7.74 (d, J = 8.03 Hz, 1 H), 7.54-7.64 (m, 2 H), 7.33-7.51 (m, 4 H), 6.75 (s, 1 H), 4.44 (s, 2 H), 3.98-4.13 (m, 2 H), 3.74-3.90 (m, 2 H), 3.38-3.50 (m, 2 H), 3.21-3.28 (m, 2 H), 2.52 (s, 3 H)

TABLE 3-continued

The following examples were prepared according to General Methods C or D

| IUPAC name | Structure | Example number MS calcd; MS ESI [M + H]+; HPLC purity at 254 nm | Yield; Appearance; Salt form |
|---|---|---|---|
| 2-(4-(3-((6-(2-chlorophenyl)-5H-pyrrolo[3,2-d]pyrimidin-2-yl)amino)phenyl)piperazin-1-yl)ethanol | 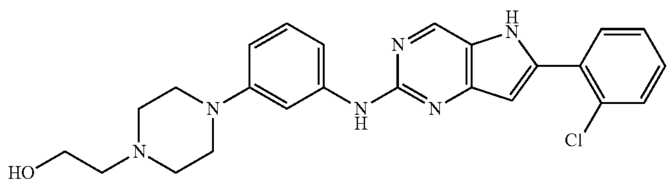 [SMILES: OCCN1CCN(c2cccc(Nc3ncc4[nH]c(-c5ccccc5Cl)cc4n3)c2)CC1] | A16; [C$_{24}$H$_{25}$ClN$_6$O + H]+ 449.18; 449.3; 98.8% | 10 mg (11%); pale yellow solid; HCl salt |

SMs: 2-chloro-6-(2-chlorophenyl)-5H-pyrrolo[3,2-d]pyrimidine (50 mg, 0.19 mol), K$_2$CO$_3$ (260 mg, 1.9 mmol), 2-(4-(3-aminophenyl)piperazin-1-yl)ethanol (63 mg, 0.28 mmol), Pd(OAc)$_2$ (4.2 mg, 0.019 mmol), dioxane (5 mL), Xantphos (21.9 mg, 0.038 mmol).
$^1$H NMR (400 MHz, CD$_3$OD) δ ppm 8.87 (s, 1 H), 7.76 (dd, J = 6.53, 2.50 Hz, 1 H), 7.67 (dd, J = 7.30, 1.60 Hz, 1 H), 7.51-7.61 (m, 2 H), 7.41 (t, J = 8.03 Hz, 1 H), 7.30 (br. s., 1 H), 7.15 (d, J = 7.78 Hz, 1 H), 7.00 (dd, J = 7.15, 0.63 Hz, 1 H), 6.89 (s, 1 H), 3.87-4.00 (m, 3 H), 3.72-3.81 (m, 1 H), 3.47-3.55 (m, 2 H), 3.34-3.45 (m, 4 H), 3.18-3.29 (m, 2 H).

| N-(4-(4-methylpiperazin-1-yl)phenyl)-6-(o-tolyl)-5H-pyrrolo[3,2-d]pyrimidin-2-amine | | A17; [C$_{24}$H$_{26}$N$_6$ + H]+ 399.23; 399.3; 95.5% | 78 mg (18%); yellow solid; HCl salt |

SMs: 2-chloro-6-(o-tolyl)-5H-pyrrolo[3,2-d]pyrimidine (243 mg, 1.0 mmol), 4-(4-methylpiperazin-1-yl)aniline (229 mg, 1.2 mmol), Pd(OAc)$_2$ (22.4 mg, 0.10 mmol), Xantphos (116 mg, 0.20 mmol), K$_2$CO$_3$ (414 mg, 3.0 mmol)
$^1$H NMR (400 MHz, CD$_3$OD) δ ppm 8.73 (s, 1 H), 7.55 (d, J = 8.03 Hz, 1 H), 7.48 (d, J = 8.53 Hz, 2 H), 7.33-7.46 (m, 3 H), 7.16 (d, J = 8.53 Hz, 2 H), 6.60 (s, 1 H), 3.86-3.94 (m, 2 H), 3.61-3.68 (m, 2 H), 3.07-3.18 (m, 2 H), 2.99 (s, 3 H), 2.49 (s, 3 H), signal due to 2H buried under the solvent peak at 3.31 ppm.

| N-(4-((4-methylpiperazin-1-yl)methyl)phenyl)-6-(o-tolyl)-5H-pyrrolo[3,2-d]pyrimidin-2-amine | | A18; [C$_{25}$H$_{28}$N$_6$ + H]+ 413.24; 413.4; 97.9% | 162 mg (36%); yellow solid; HCl salt |

SMs: 2-chloro-6-(o-tolyl)-5H-pyrrolo[3,2-d]pyrimidine (243 mg, 1.0 mmol), 4-((4-methylpiperazin-1-yl)methyl)aniline (246 mg, 1.2 mmol), Pd(OAc)$_2$ (22.4 mg, 0.10 mmol), Xantphos (116 mg, 0.20 mmol), K$_2$CO$_3$ (414 mg, 3.0 mmol)
$^1$H NMR (400 MHz, CD$_3$OD) δ ppm 8.79 (s, 1 H), 7.81 (d, J = 8.03 Hz, 2H), 7.68 (d, J = 8.78 Hz, 2 H), 7.59 (d, J = 7.78 Hz, 1 H), 7.36-7.50 (m, 3 H), 6.74 (s, 1 H), 4.45 (br. s., 2 H), 3.40-3.87 (m, 8 H), 3.02 (s, 3 H), 2.52 (s, 3 H)

| N-(3-morpholinopropyl)-6-(o-tolyl)-5H-pyrrolo[3,2-d]pyrimidin-2-amine | | A19; [C20H$_{25}$N$_5$O + H]+ 352.2; 352.3; 96.9% | 35 mg (43%); pale yellow solid; HCl salt |

SMs: 2-chloro-6-(o-tolyl)-5H-pyrrolo[3,2-d]pyrimidine (50 mg, 0.21 mmol), 3-morpholinopropan-1-amine (178 mg, 1.23 mmol), 4 M HCl in dioxane (0.10 mL)
$^1$H NMR (400 MHz, CD$_3$OD) δ ppm 8.72 (1 H, s), 7.55 (d, J = 8.03 Hz, 1 H), 7.34-7.48 (m, 3 H), 6.61 (s, 1 H), 4.01-4.11 (m, 2 H), 3.76-3.87 (m, 2 H), 3.63-3.73 (m, 2 H), 3.49-3.58 (m, 2 H), 3.26-3.31 (m, 2 H), 3.10-3.24 (m, 2 H), 2.49 (s, 3 H), 2.13-2.26 (m, 2 H)

TABLE 3-continued

The following examples were prepared according to General Methods C or D

| IUPAC name | Structure | Example number MS calcd; MS ESI [M + H]+; HPLC purity at 254 nm | Yield; Appearance; Salt form |
|---|---|---|---|
| 6-(2-chlorophenyl)-N-(3-morpholinophenyl)-5H-pyrrolo[3,2-d]pyrimidin-2-amine | 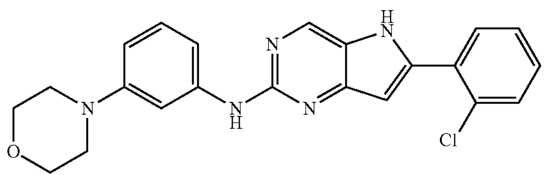 [SMILES: Clc1ccccc1-c1cc2nc(Nc3cccc(N4CCOCC4)c3)ncc2[nH]1] | A20; [C$_{22}$H$_{20}$ClN$_5$O + H]+ 406.14; 406.3; 98.1%; | 5.2 mg (3%); off white solid; free base |

SMs: 2-chloro-6-(2-chlorophenyl)-5H-pyrrolo[3,2-d]pyrimidine (120 mg, 0.45 mol), K$_2$CO$_3$ (410 mg, 3.0 mmol), 3-morpholinoaniline (129 mg, 0.72 mmol), Pd(OAc)$_2$ (10 mg, 0.044 mmol), dioxane (20 mL), Xantphos (54 mg, 0.093 mmol).
$^1$H NMR (400 MHz, CD$_3$OD) δ ppm 8.61 (s, 1 H), 7.68-7.73 (m, 1 H), 7.58-7.63 (m, 1 H), 7.44-7.48 (m, 2 H), 7.42 (s, 1 H), 7.14-7.25 (m, 2 H), 6.70 (s, 1 H), 6.63 (d, J = 7.30 Hz, 1 H), 3.83-3.90 (m, 4 H), 3.14-3.21 (m, 4 H).

| (1r,4r)-4-((6-(o-tolyl)-5H-pyrrolo[3,2-d]pyrimidin-2-yl)amino)cyclohexanol | | A21; [C$_{19}$H$_{22}$N$_4$O + H]+ 323.19; 323.3; 98.0% | 25 mg (37%); white solid; free base |

SMs: 2-chloro-6-(o-tolyl)-5H-pyrrolo[3,2-d]pyrimidine (50 mg, 0.21 mmol), trans-4-aminohexanol (145 mg, 1.3 mmol), 4 M HCl in dioxane (0.10 mL)
$^1$H NMR (400 MHz, DMSO-d$_6$) δ ppm 11.30 (br. s., 1 H), 8.40 (s, 1 H), 7.47-7.54 (m, 1 H), 7.28-7.39 (m, 3 H), 6.35 (s, 1 H), 6.07 (d, J = 7.53 Hz, 1 H), 4.49-4.56 (m, 1 H), 3.60-3.73 (m, 1 H), 3.36-3.46 (m, 1 H), 2.44 (s, 3 H), 1.88-1.98 (m, 2 H), 1.77-1.87 (m, 2 H), 1.20-1.29 (m, 4 H)

| (1s,4s)-4-((6-(o-tolyl)-5H-pyrrolo[3,2-d]pyrimidin-2-yl)amino)cyclohexanol | | A22; [C$_{19}$H$_{22}$N$_4$O + H]+ 323.19; 323.3; 96.8% | 11.1 mg (16%); white solid; free base |

SMs: 2-chloro-6-(o-tolyl)-5H-pyrrolo[3,2-d]pyrimidine (50 mg, 0.21 mmol), cis-4-aminohexanol (145 mg, 1.3 mmol), 4 M HCl in dioxane (0.10 mL)
$^1$H NMR (400 MHz, DMSO-d$_6$) δ ppm 11.30 (s, 1 H), 8.41 (s, 1 H), 7.46-7.54 (m, 1 H), 7.26-7.40 (m, 3 H), 6.34 (s, 1 H), 6.06 (d, J = 7.78 Hz, 1 H), 4.29-4.36 (m, 1 H), 3.68-3.81 (m, 2 H), 2.44 (s, 3 H), 1.44-1.74 (m, 8 H)

| N-(tetrahydro-2H-pyran-4-yl)-6-(o-tolyl)-5H-pyrrolo[3,2-d]pyrimidin-2-amine | | A23; [C$_{18}$H$_{20}$N$_4$O + H]+ 309.17; 309.3; 98.0% | 14.1 mg (22%); white solid; free base |

SMs: 2-chloro-6-(o-tolyl)-5H-pyrrolo[3,2-d]pyrimidine (50 mg, 0.21 mmol), 4-aminotetrahydropyran (127 mg, 1.3 mmol), 4 M HCl in dioxane (0.10 mL)
$^1$H NMR (400 MHz, CD$_3$OD) δ ppm 8.42 (s, 1 H), 7.50 (d, J = 7.28 Hz, 1 H), 7.25-7.38 (m, 3 H), 6.36 (s, 1 H), 3.94-4.08 (m, 3 H), 3.52-3.63 (m, 2 H), 2.47 (s, 3 H), 1.98-2.08 (m, 2 H), 1.50-1.67 (m, 2 H)

| N-((tetrahydro-2H-pyran-4-yl)methyl)-6-(o-tolyl)-5H-pyrrolo[3,2-d]pyrimidin-2-amine | | A24; [C$_{19}$H$_{22}$N$_4$O + H]+ 323.19; 323.3; 98.9% | 16.5 mg (32%); white solid; free base |

SMs: 2-chloro-6-(o-tolyl)-5H-pyrrolo[3,2-d]pyrimidine (40 mg, 0.21 mmol), (tetrahydro-2H-pyran-4-yl)methanamine (113 mg, 0.99 mmol), 4 M HCl in dioxane (0.080 mL)
$^1$H NMR (400 MHz, CD$_3$OD) δ ppm 8.41 (s, 1 H), 7.50 (d, J = 7.53 Hz, 1 H), 7.26-7.38 (m, 3 H), 6.36 (s, 1 H), 3.91-4.00 (m, 2 H), 3.37-3.47 (m, 2 H), 2.47 (s, 3 H), 1.88-2.01 (m, 1 H), 1.71-1.80 (m, 2 H), 1.28-1.42 (m, 2 H). signal due to 2H buried under the solvent peak at 3.31 ppm.

TABLE 3-continued

The following examples were prepared according to General Methods C or D

| IUPAC name | Structure | Example number MS calcd; MS ESI [M + H]+; HPLC purity at 254 nm | Yield; Appearance; Salt form |
| --- | --- | --- | --- |
| 6-(2-methoxyphenyl)-N-(3-morpholinophenyl)-5H-pyrrolo[3,2-d]pyrimidin-2-amine | 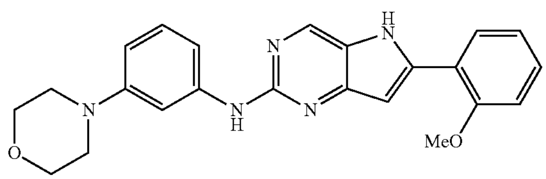 [SMILES: COc1ccccc1-c1cc2nc(Nc3cccc(N4CCOCC4)c3)ncc2[nH]1] | A25; [C₂₃H₂₃N₅O₂ + H]+ 402.2; 402.3; 96.5% | 43 mg (52%); orange solid; HCl salt |
| N-((1-morpholino-cyclopentyl)methyl)-6-(o-tolyl)-5H-pyrrolo[3,2-d]pyrimidin-2-amine | | A26; [C₂₃H₂₉N₅O + H]+ 392.25; 392.4; 96.0% | 44 mg (52%); beige solid; HCl salt |

SMs: 2-chloro-6-(2-methoxyphenyl)-5H-pyrrolo[3,2-d]pyrimidine (50 mg, 0.19 mmol), 3-morpholinoaniline (137 mg, 0.77 mmol), 4 M HCl in dioxane (0.10 mL)
¹H NMR (400 MHz, CD₃OD) δ ppm 8.73 (s, 1 H), 7.92-7.99 (m, 1 H), 7.68-7.75 (m, 1 H), 7.54-7.61 (m, 1 H), 7.47-7.54 (m, 1 H), 7.26-7.37 (m, 2 H), 7.14-7.23 (m, 2 H), 7.02 (s, 1 H), 4.09 (s, 3 H), 3.95-4.02 (m, 4 H), 3.44-3.52 (m, 4 H)

SMs: 2-chloro-6-(o-tolyl)-5H-pyrrolo[3,2-d]pyrimidine (50 mg, 0.20 mmol), (1-morpholinocyclopentyl)methanamine (151 mg, 0.82 mmol), 4 M HCl in dioxane (0.10 mL)
¹H NMR (400 MHz, CD₃OD) δ ppm 8.74 (br. s., 1 H), 7.57 (d, J = 7.28 Hz, 1 H), 7.33-7.51 (m, 3 H), 6.68 (s, 1 H), 4.01-4.18 (m, 4 H), 3.83-3.97 (m, 2 H), 3.62-3.77 (m, 2 H), 3.44-3.58 (m, 2 H), 2.51 (s, 3 H), 2.02-2.20 (m, 4 H), 1.81-1.99 (m, 4 H)

Example B: RIPK2 Inhibition Assay

Active RIPK2 was purchased from Life Technologies as His-tagged of catalytic domain (amin acids 1-299) of human RIPK2 kinase expressed in insect cells Amino terminal 6 histidine, sumo tagged human TTK (residues 1-275) was expressed in *E. coli*, and purified to >95% homogeneity by Ni²⁺ agarose, gel filtration, and ion exchange chromatography.

RIPK2 activity was measured using an indirect ELISA detection system. His-RIPK2 (0.6 nM) was incubated in the presence of 6 μM ATP (Sigma cat #A7699), 20 mM Hepes, pH 7.5, 1 mM EGTA, 2.5 mM MgCl₂, 2.5 mM MnCl₂ and 0.01% Triton X-100 in a 96 well microtitre plate pre-coated with amino terminal 6 histidine, sumo tagged TTK (amino acid residues 1-275). The reaction was allowed to proceed for 30 minutes, followed by 5 washes of the plate with Wash Buffer (phosphate buffered saline supplemented with 0.2% Tween 20), and incubation for 30 minutes with a 1:3000 dilution of primary antibody (Cell Signaling cat #9381). The plate was washed 5 times with Wash Buffer, incubated for 30 minutes in the presence of secondary antibody coupled to horse radish peroxidase (BioRad cat #1721019, 1:3000 concentration), washed an additional 5 times with Wash Buffer, and incubated in the presence of TMB substrate (Sigma cat #T0440). The colorimetric reaction was allowed to continue for 5 minutes, followed by addition of stop solution (0.5 N H₂SO₄), and quantified by detection at 450 nm with either a monoChromatic or filter based plate reader (Molecular Devices M5 or Beckman DTX880, respectively).

Compound inhibition was determined at either a fixed concentration (10 μM) or at a variable inhibitor concentration (typically 50 μM to 0.1 μM in a 10 point dose response titration). Compounds were pre-incubated in the presence of enzyme for 15 minutes prior to addition of ATP and the activity remaining quantified using the above described activity assay. The % Inhibition of a compound was determined using the following formula; % Inhibition=100×(1−(experimental value−background value)/(high activity control−background value)). The IC₅₀ value was determined using a non-linear 4 point logistic curve fit (XLfit4, IDBS) with the formula; (A+(B/(1+((x/C)^D)))), where A=background value, B=range, C=inflection point, D=curve fit parameter.

In Table 1 presents IC₅₀ value ranges for compound examples indicated as "A," "B," and "C," for values less than or equal to 0.1 μM; those greater than 0.1 μM and less than or equal to 0.5 μM; and those greater than 0.5 μM, respectively.

TABLE 1

In vitro activity against RIPK2 data for the example compounds of the invention.

| Example | RIPK2 IC$_{50}$ range |
|---|---|
| A1 | C |
| A2 | A |
| A3 | A |
| A4 | A |
| A5 | C |
| A6 | A |
| A7 | A |
| A8 | A |
| A9 | A |
| A10 | C |
| A11 | A |
| A12 | A |
| A13 | B |
| A14 | C |
| A15 | A |
| A16 | A |
| A17 | A |
| A18 | A |
| A19 | C |
| A20 | A |
| A21 | B |
| A22 | C |
| A23 | C |
| A24 | B |
| A25 | B |
| A26 | C |

Example C: Activity Against Cancer Cell Line for Example Compounds of the Invention Breast cancer cells (MDA-MB-231 and MDA-MB-468), colon cancer cells (HCT116 and HT-29) and ovarian cancer cells (SKOV-3 and OVCAR-3) were seeded (1000 to 4000 in 80 μL per well depending on the cell growth rate) into 96 well plates 24 hours before compound overlay. Compounds were prepared as 10 mM stock solutions in 100% DMSO which were diluted with DMEM (Dulbecco's Modified Eagle's Medium) cell growth Medium (Invitrogen, Burlington, ON, Canada) containing 10% FBS (Fetal Bovine Serum) to concentrations ranging from 50 nM to 250 μM. Aliquots (20 μL) from each concentration were overlaid to 80 μL of the pre-seeded cells in the 96 well plates to make final concentrations of 10 nM to 50 μM. The cells were cultured for 5 days before the Sulforhodamine B assay (SRB) was performed to determine the compound's cell growth inhibition activity.

The cells are fixed in situ by gently aspirating off the culture media and adding 50 μL ice cold 10% trichloroacetic acid per well and incubate at 4° C. for 30-60 min. The plates are washed with H$_2$O five times and allowed to air dry for 5 min Addition of 50 μL 0.4% (w/v) SRB solution in 1% (v/v) acetic acid to each well and incubation for 30 min at rt completes the staining reaction. Following staining, plates are washed four times with 1% acetic acid to remove unbound dye and then allowed to air dry for 5 min. The stain is solubilized with 100 μL of 10 mM Tris pH 10.5 per well. Absorbance is read at 570 nm. The percentage (%) of relative growth inhibition was calculated by comparing to DMSO treated only cells (100%). GI$_{50}$'s were determined for compounds with cytotoxic activity. The GI$_{50}$ was calculated using GraphPad PRISM software (GraphPad Software, Inc., San Diego, Calif., USA). GI$_{50}$ (growth inhibition) is the compound concentration that causes 50% inhibition of cell growth.

In Table 2 lists GI$_{50}$ value ranges for compound examples against breast cancer cell lines (MDA-MB-231, MDA-MB-468), colon cancer cell lines (HCT116, HT-29) and ovarian cancer cell lines (OVCAR-3, SKOV-3) are given. The example compounds demonstrated varying growth inhibition/cell killing activity against cells of breast cancer, colon cancer, and ovarian cancer. The GI$_{50}$ ranges are indicated as "A," "B," and "C," for values less than or equal to 1 μM; those greater than 1 μM and less than or equal to 10 μM; and those greater than 10 μM, respectively.

TABLE 2

In vitro cell antiproliferative activity data for Example Compounds of the Invention

| | Breast GI$_{50}$ range | | Colon GI$_{50}$ range | | Ovarian GI$_{50}$ range | |
|---|---|---|---|---|---|---|
| Example | MDA-MB-231 | MDA-MB-468 | HCT116 | HT29 | OVCAR-3 | SKOV-3 |
| A3 | A | A | A | A | A | A |
| A8 | C | ND | C | C | C | C |
| A12 | B | B | B | B | A | A |
| A13 | A | A | A | A | A | A |
| A7 | B | ND | B | B | B | B |
| A2 | B | B | B | B | B | B |
| A4 | A | A | A | A | A | B |
| A6 | B | ND | B | A | A | A |
| A9 | C | ND | B | A | A | A |

Example D: In Vivo Response of HCT116 Xenografts to Treatment with Exemplified Compounds of the Invention HCT116 colon cancer cells were purchased from ATCC (American Type Culture Collections) and cultured in DMEM (Dulbecco's Modified eagle medium—purchased from GIBCO) supplemented with 10% fetal calf serum. Five million cells were injected subcutaneously in the right flank of 6-8 week old male CB-17 SCID mice. When the mean tumor volume reached 80-120 mm$^3$, mice were randomized into 5 groups (n=5) and received either vehicle (10% NMP, 40% PEG, 50% H$_2$O) or compound at the doses indicated.

Tumor volume and body weight were measured three times weekly. Tumor volume was calculated by the following formula: $x^2y/2$. Percent tumor growth inhibition after initiation of treatment with compound was calculated by: TGI=100×1−(tumor volume$_{final}$−tumor volume$_{initial}$ for compound treated group)/(tumor volume$_{final}$−tumor volume$_{initial}$ for compound control group).

Test results are shown in FIG. 1. It demonstrates that compound Example A3 was well tolerated, with less than 6% mean body weight loss in the treated arms compared to control (control loses 2.6%, 92 mg/kg loses 7.8%).

Example E: Effect of Example A3 on Cytokine Production by Dendritic Cells

Figure 2C:
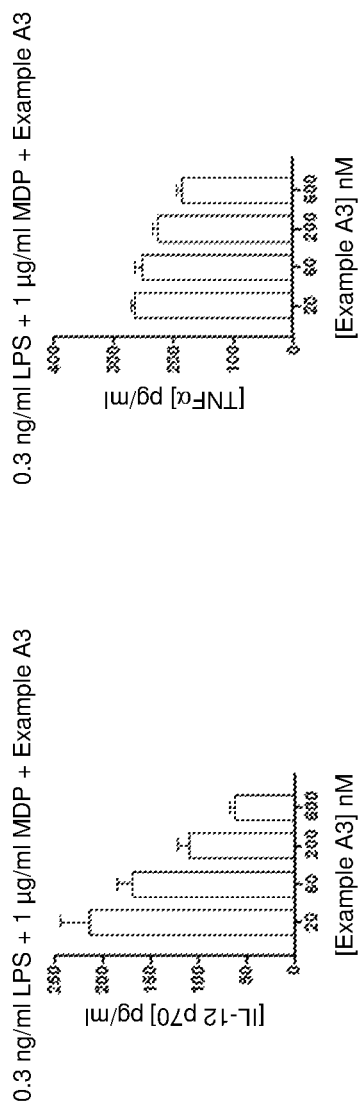

IL-12-yellow fluorescent protein (YFP) reporter mouse bone marrow dendritic cells were stimulated for 24 hours with 0.3 ng/ml LPS±1 μg/ml MDP (i.e., NOD2 agonist) in the presence of Example A3 (FIG. 2A). IL-12-yellow fluorescent protein (YFP) reporter mouse bone marrow dendritic cells were stimulated for 24 hours with 0.3 μg/ml Pam3Cys±1 μg/ml MDP (i.e., NOD2 agonist) in the presence of Example A3 (FIG. 2B). Flow cytometric analysis showed that Example A3 caused a dose-dependent reduction in the mean fluorescence intensity YFP (i.e., the amount of IL-12; left panels). This effect of Example A3 was MDP-dependent and suggests that it involves blocking NOD2-RIPK2 responses. Example A3 had a minimal effect on the percentage of YFP positive cells (i.e., the percentage of IL-12 positive cells; middle panels), and no measurable effect on cell viability as assessed by 7AAD exclusion (right panels). Data are represented as the mean±SEM of triplicate measurements. Levels of IL-12 p70 (FIG. 2C, left panel) and TNFα (FIG. 2C, right panel) in the cell culture supernatants from A were measured by ELISA techniques with commercially available kits. Example A3 caused a dose-dependent reduction in the levels of both cytokines. Data are represented as the mean±SEM of triplicate measurements.

What is claimed is:

1. A method for treating a subject with cancer, comprising:
administering to the subject an effective amount of a compound represented by Formula (I):

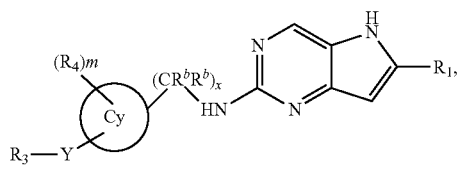

or a pharmaceutically acceptable salt thereof, wherein:
Cy is cycloaliphatic, heterocyclyl, aryl, or heteroaryl;
Y is absent, —$CR^bR^b$—, —O—, —$NR^b$—, —$S(O)_n$—;
$R_1$ is cycloaliphatic, heterocyclyl, aryl or heteroaryl, each of which is optionally substituted with 1 to 3 groups individually represented by $R^a$;
$R_3$ is H, heterocyclyl or heteroaryl optionally substituted with 1 to 3 groups selected from —F, —Cl, —Br, I, —CN, —$NO_2$, —$OR^b$, —$C_1$-$C_4$alkyl, —($C_1$-$C_3$)alkylene-$OR^b$, —($C_1$-$C_3$)alkylene-$NR^bR^b$, —$C_1$-$C_4$haloalkyl, —$C_1$-$C_4$haloalkoxy, ($C_3$-$C_8$)cycloalkyl, —$NR^bR^b$, —C(=O)$NR^bR^b$, —$NR^b$(C=O)$NR^bR^b$, —$S(O)_nNR^bR^b$, C(=O)$OR^b$, —OC(=O)$OR^b$, —$S(O)_nR^b$, —$NR^bS(O)_nR^b$, —C(=S)$OR^b$, —O(C=S)$R^b$, —$NR^bC(=O)R^b$, —C(=S)$NR^bR^b$, —$NR^bC(=S)R^b$, —$NR^b(C=O)OR^b$, —O(C=O)$NR^bR^b$, —$NR^b(C=S)OR^b$, —O(C=S)$NR^bR^b$, —$NR^b(C=S)NR^bR^b$, —C(=S)$R^b$ or —C(=O)$R^b$;
each $R_4$ is independently selected from —F, —Cl, —Br, I, —CN, —$NR^bR^b$, —$OR^b$, —$C_1$-$C_4$alkyl, —($C_1$-$C_3$)alkylene-$OR^b$, —($C_1$-$C_3$)alkylene-$NR^bR^b$, —$C_1$-$C_4$haloalkyl, or —$C_1$-$C_4$haloalkoxy;
each $R^a$ is independently selected from —F, —Cl, —Br, I, —CN, $OR^b$, —$C_1$-$C_4$alkyl, ($C_2$-$C_6$)alkenyl, ($C_2$-$C_6$)alkynyl, —$C_1$-$C_4$haloalkyl, —$C_1$-$C_4$haloalkoxy, —($C_1$-$C_3$)alkylene-$OR^b$, or —($C_1$-$C_3$)alkylene-$NR^bR^b$;
each $R^b$ is independently —H or —$C_1$-$C_4$alkyl;
x is 0, 1, 2, 3, or 4;
each m is independently 0, 1, 2, or 3; and
each n is independently 0, 1, or 2,
wherein the cancer is breast cancer, colon cancer, or ovarian cancer.

2. The method of claim 1, wherein the compound is represented by structural formula (II):

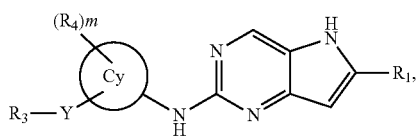

or a pharmaceutically acceptable salt thereof.

3. The method of claim 2, wherein the compound is represented by structural formula (III):

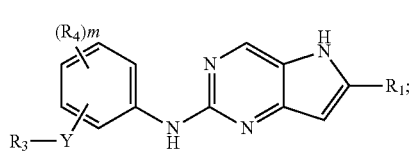

or a pharmaceutically acceptable salt thereof.

4. The method of claim 3, wherein $R_1$ is optionally substituted phenyl, optionally substituted cyclopentyl, optionally substituted cyclohexyl, optionally substituted thienyl, optionally substituted pyridinyl, optionally substituted thiazolyl, optionally substituted pyrrolyl, optionally substituted imidazolyl, optionally substituted furanyl, optionally substituted oxazolyl, optionally substituted isoxazolyl, optionally substituted pyrazolyl, optionally substituted isothiazolyl, optionally substituted pyrimidinyl, optionally substituted pyrazinyl, optionally substituted pyridazinyl, optionally substituted oxadiazolyl, optionally substituted tetrahydropyranyl, optionally substituted triazolyl, or optionally substituted thiadiazolyl.

5. The method of claim 4, wherein $R_1$ is optionally substituted phenyl, optionally substituted cyclopentyl, optionally substituted thienyl, or optionally substituted tetrahydropyranyl.

6. The method of claim 5, wherein $R_3$ is optionally substituted monocyclic heterocyclyl or optionally substituted monocyclic heteroaryl.

7. The method of claim 6, wherein m is 0.

8. The method of claim 7, wherein $R_3$ is optionally substituted azetidinyl, optionally substituted morpholinyl, optionally substituted piperazinyl, optionally substituted piperidinyl, optionally substituted tetrahydropyranyl, optionally substituted pyrrolidinyl, optionally substituted thiomorpholinyl, optionally substituted tetrahydropyranyl, optionally substituted tetrahydrofuranyl, optionally substituted homomorpholinyl, optionally substituted homopiperazinyl, optionally substituted thiomorpholine dioxide, or optionally substituted thiomorpholine oxide.

9. The method of claim 8, wherein $R_3$ is optionally substituted morpholinyl, optionally substituted piperazinyl, optionally substituted piperidinyl, or optionally substituted thiomorpholinyl.

10. The method of claim 9, wherein the compound is represented by the following structural formula:

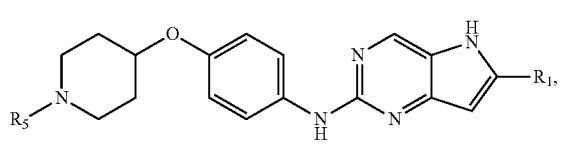

or a pharmaceutically acceptable salt thereof, wherein R$_5$ is —C$_1$-C$_4$alkyl or —(C$_1$-C$_3$)alkylene-OR$^b$.

11. The method of claim 9, wherein the compound is represented by the following structural formula:

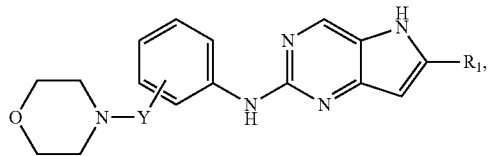

or a pharmaceutically acceptable salt thereof, wherein Y is absent or —CH$_2$—; and Y is attached to the meta or para position of the phenyl ring.

12. The method of claim 9, wherein the compound is represented by the following structural formula:

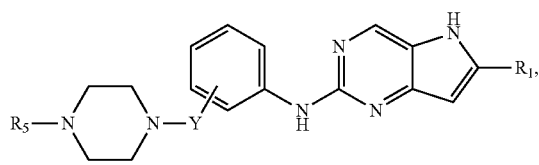

or a pharmaceutically acceptable salt thereof, wherein R$_5$ is —H, C$_1$-C$_4$alkyl, —(C$_1$-C$_3$)alkylene-OR$^b$; Y is absent or —CH$_2$—; and Y is attached to the meta or para position of the phenyl ring.

13. The method of claim 9, wherein R$_1$ is

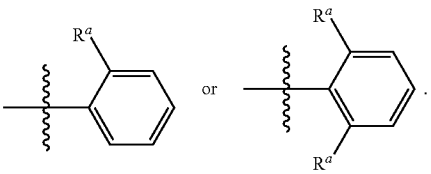

14. The method of claim 13, wherein each R$^a$ is independently selected from —F, —Cl, or —CH$_3$.

15. The method of claim 1, wherein the compound is

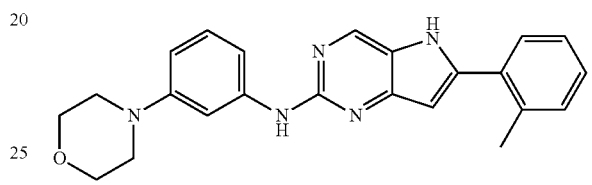

* * * * *